(12) United States Patent
Schwendeman et al.

(10) Patent No.: US 6,743,446 B2
(45) Date of Patent: Jun. 1, 2004

(54) METHODS FOR STABILIZING BIOLOGICALLY ACTIVE AGENTS ENCAPSULATED IN BIODEGRADABLE CONTROLLED-RELEASE POLYMERS

(75) Inventors: Steven P. Schwendeman, Ann Arbor, MI (US); Gaozhong Zhu, Arlington, MA (US); Hanne Bentz, Newark, CA (US); Jeffrey A. Hubbell, Zumilon (CH); Wenlei Jiang, Randolph, NJ (US); Anna Shenderova, Ann Arbor, MI (US); Jichao Kang, Ann Arbor, MI (US)

(73) Assignee: The Ohio State University Research Foundation, Columbus, OH (US)

( * ) Notice: Subject to any disclaimer, the term of this patent is extended or adjusted under 35 U.S.C. 154(b) by 98 days.

(21) Appl. No.: 09/738,961

(22) Filed: Dec. 15, 2000

(65) Prior Publication Data

US 2002/0009493 A1 Jan. 24, 2002

Related U.S. Application Data

(60) Provisional application No. 60/170,983, filed on Dec. 15, 1999.

(51) Int. Cl.[7] .................................................. A61K 9/14
(52) U.S. Cl. .................... 424/486; 424/489; 424/484
(58) Field of Search ................................ 424/486, 489, 424/484

(56) References Cited

U.S. PATENT DOCUMENTS

| | | | |
|---|---|---|---|
| 5,413,797 A | 5/1995 | Khan et al. | |
| 5,643,605 A | * 7/1997 | Cleland et al. | ............. 424/489 |
| 5,654,010 A | 8/1997 | Johnson et al. | |
| 5,656,297 A | 8/1997 | Bernstein et al. | |
| 5,912,015 A | 6/1999 | Bernstein et al. | |

OTHER PUBLICATIONS

"The stability and immunogenicity of a protein antigen encapsulated in biodegradable microparticles based on blends of lactide polymers and polyethylene glycol" by Lavelle, et al., *Vaccine*, 17, pp. 512–529, 1999.

"Stabilization of tetanus and diphtheria toxoids against moisture–induced aggregation" by Schwendeman, et al., *Proc. Natl. Acad. Sci, USA*, vol. 92, pp. 11234–11238, Nov. 1995.

"Stabilization of Proteins Encapsulated in Cylindrical Poly-(lactide–co–glycolide) Implants: Mechanism of Stabilization by Basic Additives" by Zhu, et al., *Pharmaceutical Research*, vol. 17, No. 3, 2000, pp. 350–356.

"Stabilization of Vinca Alkaloids Encapsulated in Poly(lactide–co–glycolide) Microspheres" by Marinina, et al., *Pharmaceutical Research*, vol. 17, No. 6, 2000, pp. 677–682.

Chapter 48 "Gastric Antacids and Digestants" by Harvey, *The Pharmacological Basis of Therapeutics, Fourth Edition*, The McMillan Company, London, Toronto.

* cited by examiner

*Primary Examiner*—Thurman K. Page
*Assistant Examiner*—Blessing Fubara
(74) *Attorney, Agent, or Firm*—Calfee, Halter & Griswold LLP

(57) ABSTRACT

Methods for reducing or inhibiting the irreversible inactivation of water-soluble biologically active agents in biodegradable polymeric delivery systems which are designed to release such agents over a prolonged period of time, such as PLGA delivery systems are provided. The method comprises preparing a PLGA delivery systems whose microclimate, i.e. the pores where the active agent resides, uniformly or homogenously maintain a pH of between 3 and 9, preferably between 4 and 8, more preferably between 5 and 7.5 during biodegradation. Depending on the size of the delivery system, and the initial bulk permeability of the polymer, this result is achieved by (a) incorporating a water-soluble carrier into the delivery system, (b) incorporating a select basic additive (or antacid) into the delivery system, (c) incorporating both a water soluble carrier and a select basic additive into the delivery system, (d) adding a pore forming molecule for increasing the rate of release of low molecular weight monomers and oligomers into the delivery system, (e) using a PLGA polymer with reduced glycolide content, i.e. PLGA with from 100% to 75% lactide and 0 to 25% glycolide) (f) using a microencapsulation method that yields a more extensive pore-network, e.g. oil-in-oil emulsion-solvent extraction as opposed to water-in-oil-in water-solvent evaporation method, and (g) combinations thereof.

31 Claims, No Drawings

METHODS FOR STABILIZING BIOLOGICALLY ACTIVE AGENTS ENCAPSULATED IN BIODEGRADABLE CONTROLLED-RELEASE POLYMERS

This application claims priority from provisional application Ser. No. 60/170,983, filed Dec. 15, 1999.

This invention was made at least in part with government support under National Institutes of Health Grant DE 12183. The government has certain rights in the invention.

BACKGROUND

Since the concept of protein or drug delivery from polymers was first introduced, research efforts have focused on developing polymer formulations that would be widely applicable for delivery of biologically active agents, such as proteins, peptides, oligonucleotides, DNA, low molecular weight drugs and vaccine antigens. Efforts to this end have intensified recently since hundreds of recombinant proteins and other biotechnological drugs and vaccine antigens are in the pipeline for FDA approval, and the current method of protein delivery generally requires injections on a daily basis. Frequent dosing is clinically undesirable due to patient discomfort, psychological distress, and poor compliance for administering self-injections. To reduce injection frequency, peptide and protein drugs are encapsulated in biodegradable polymers, which are processed into a form that is easily administered through a syringe needle. Current preparations on the market for the delivery of small peptides can reduce the frequency of injections to once every 1–3 months depending on the size and dose of the polymer implant. This incubation time, for which a large globular protein must remain encapsulated in the polymer at physiological temperature, poses significant challenges to retain both the structural integrity and the biological activity of the protein.

Two injectable polymer configurations are currently used to deliver peptides and proteins: spherical particles on the micrometer scale (~1–100 µm), which are commonly referred to as "microspheres", and single cylindrical implants on the millimeter scale (~0.8–1.5 mm in diameter), which we term "millicylinders". Both configurations are prepared from the biocompatible copolymer class, poly(lactide-co-glycolide) (PLGA) commonly used in resorbable sutures, and each configuration has distinct advantages and disadvantages.

Once injected into the body, these polymer implants slowly release the biologically active agents, thereby providing desirable levels of the agent over a prolonged period of time. Because of its safety, FDA approval and biodegradability, the poly(lactide-co-glycolides) (PLGAs) are the most common polymer class used for preparing biodegradable delivery systems for biologically active agents. Unfortunately, the microenvironment in PLGA surrounding the encapsulated agent can become highly acidic, causing many of these agents to lose their biological activity. Accordingly, it is desirable to modify the methods that are currently used to prepare polymeric delivery systems which liberate acids during biodegradation, such as PLGA, and to thereby produce a polymeric implant that is capable of releasing the biologically active agent over a prolonged period of time and maintaining the stability of the biologically active agent that is retained in the delivery system during nonenzymatic hydrolysis, hereinafter referred to as "biodegradation" of such a system. Such methods would also be useful for preparing implants that are made from polymers that contain acid that slowly dissolves and lowers the pH of the microenvironment surrounding the encapsulated agent

SUMMARY OF THE INVENTION

The present invention provides new methods for reducing or inhibiting the irreversible inactivation of water-soluble biologically active agents in biodegradable polymeric delivery systems which are designed to release such agents over a prolonged period of time, such as PLGA delivery systems. In accordance with the present invention, it has been discovered that, in many instances, the acids that are produced during biodegradation of PLGA can induce an irreversible inactivation or instability of biologically active agents, such as for example proteins, drugs, oligonucleotides and vaccine antigens. It has also been determined that the addition of certain antacids, such as for example $MgOH_2$, to the system will not significantly reduce the acid-induced instability of the biologically active unless the polymer is prepared in a manner which results in the formation of an interconnected network of pores within the polymer. It has also been discovered that the acid-induced instability of biologically active agents encapsulated in PLGA delivery can be inhibited or significantly reduced by preparing PLGA delivery systems whose microclimate, i.e. the pores where the active agent resides, uniformly or homogenously maintain a pH of between 3 and 9, preferably between 4 and 8, more preferably between 5 and 7.5 during biodegradation. Depending on the size of the delivery system, i.e., the weight average particle diameter and the initial bulk permeability of the polymer, this result is achieved by (a) incorporating a water-soluble carrier into the delivery system, (b) incorporating a select basic additive (or antacid) into the delivery system, (c) incorporating both a water soluble carrier and a select basic additive into the delivery system, (d) adding a pore forming molecule for increasing the rate of release of low molecular weight monomers and oligomers into the delivery system, (e) using a PLGA polymer with reduced glycolide content, i.e. PLGA with from 100% to 75% lactide and 0 to 25% glycolide) (f) using a microencapsulation method that yields a more extensive pore-network, e.g. oil-in-oil emulsion-solvent extraction as opposed to water-in-oil-in water-solvent evaporation method, and (g) combinations thereof.

The present invention also relates to PLGA delivery systems prepared by the present method. Such delivery systems have a low porosity (e.g. <50%) and a uniform morphology (e.g. spherical or cylindrical usually with smooth or uniformly rough surfaces, and when particulate, all particles are similar in external and internal appearance under the scanning electron microscope. In addition, the PLGA delivery systems of the present invention have a low initial burst release (e.g. <50% of the drug is released during the 1st hour of biodegradation) Most importantly, during biodegradation, the present PLGA delivery systems maintain a relatively homogenous microclimate pH greater than 3 and less than 9, preferably greater than 4 and less than 8, more preferably greater than 5 and less than 7.5, so that less than 15% of the combined released and residual encapsulated test protein bovine serum albumin forms nonconvalent, water-insoluble aggregates when incubated in a physiological buffer solution for 4 weeks at 37° C.

In certain embodiments, the PLGA delivery system comprises bone morphogenetic protein-2, vincristine sulfate, fibroblast growth factor, or tissue plasminogen activator.

DETAILED DESCRIPTION OF THE INVENTION

The present invention provides methods of preparing PLGA delivery systems which stabilize the soluble biologically active agents that are encapsulated therein. As used herein, the term stabilize refers to an improvement in the stability of the encapsulated agent, which is necessary to approach or achieve a stable state. A stable biologically active agent as used herein refers to a biologically active agent such as a protein, peptide, oligonucleotide, low-molecular weight drug, or vaccine antigen that retains at least 80%, preferably 90%, of its original structure and/or biological activity during its release from the PLGA delivery system. During biodegradation of PLGA delivery systems, soluble agents often undergo acid-induced irreversible instability. Such instability may result from noncovalent aggregation of the agent, peptide-bond hydrolysis, deamidation, isomerization, covalent aggregation, deformylation, depurination, etc. Each of these acid-induced physical or chemical alterations can be monitored using standard techniques known in the art. For example, aggregation can be monitored by loss of solubility, SDS-PAGE, and or size-exclusion chromatography.

The methods of the present invention also provide controlled release PLGA delivery systems. As used herein, controlled release means the release kinetics are engineered into the system such that the agent is released in a manner controlled by the system itself or its surroundings, preferably the system itself. Such controlled release requires that the agent is not all released within a short period of time, e.g., less than one hour, after injection or implantation of the system in a subject. Preferably the agent is released from the implanted system over a prolonged period of time, e.g. 3 days to 1 year. In some cases, the delivery system is designed to release the agent slowly and continuously over this prolonged period of time. In other instances the delivery system is designed to release the agent in multiple phases.

Stabilization of the encapsulated agent is achieved by providing a delivery system whose microclimate, i.e. the pores where the active agent resides, uniformly or homogeneously maintain a pH of greater than 3 and less than 8, preferably greater than 4 and less than 8, more preferably from 5 to 7.5 during biodegradation. To determine if the method has provided a polymeric delivery system whose microclimate homogenously maintains a pH of between 3 and 8, 1% w/w BSA is dispersed in the polymer solution during manufacture by the chosen method and the extent of aggreagation of this protein is assayed after 4 weeks of incubation of the polymeric delivery system in phosphate buffered saline with 0.02% Tween 80 at 37° C. If the amount of residual BSA that has formed water insoluble noncovalent aggregates (i.e., soluble in 6 M guanidine hydrochloride or 6 M urea) is less than or equal to 15% of the total BSA in the prepared polymer dosage form, the method has produce a polymeric delivery system whose microclimate homogeneously maintains a pH of between 3 and 8.

One method for preparing a delivery system which stabilizes the agent encapsulated therein during biodegradation comprises adding a poorly soluble, mildy strong basic additive to a solution comprising the biologically active agent and the polymer. Except for $CaOH_2$, the basic additive has a solubility and basicity comparable to the solubility and basicity of the compounds shown in Table I below.

TABLE 1

Solubility and basicity of basic salts.

| Salts | $pK_{sp}$[a] | Solubility[b] | pH of saturated solution[c] | Addition of 100 µl of 1 N HCl[d] |
|---|---|---|---|---|
| $Ca(OH)_2$ | 5.26 | $1.11 \times 10^{-2}$ | 12.40 | 12.20 |
| $CaCO_3$ | 8.42 | $6.17 \times 10^{-5}$ | 9.26 | 6.07 |
| $Ca_3(PO_4)_2$ | 26.0 | $3.12 \times 10^{-11}$ | 7.77 | 3.71 |
| $Mg(OH)_2$ | 10.74 | $1.66 \times 10^{-4}$ | 9.76 | 8.99 |
| $MgCO_3$ | 5.00 | $3.16 \times 10^{-3}$ | 9.75 | 9.01 |
| $Zn(OH)_2$ | 15.68 | $3.74 \times 10^{-6}$ | 8.85 | 5.86 |
| $ZnCO_3$ | 10.78 | $4.07 \times 10^{-6}$ | 7.34 | 5.36 |
| $Zn_3(PO_4)_2$ | 32.0 | $1.24 \times 10^{-13}$ | 6.82 | 1.53 |

[a]Lange's Handbook of Chemistry, Ed. John A. Dean, 11th edition, 1973.
[b]Solubility was calculated based on $pK_{sp}$ values;
[c]pH was measured after excess basic salts were suspended in 10 ml of water and incubation was continued at 37° C. for 7 days;
[d]pH was measured after the acid was added to the above suspension and incubation was continued at 37° C. for 3 days.

Suitable basic additives are magnesium carbonate, magnesium hydroxide, magnesium oxide, magnesium trisilicate, zinc carbonate, zinc hydroxide, zinc phosphate, aluminum hydroxide, basic aluminum carbonate, dihyroxyaluminum sodium carbonate, dihydroxyaluminum aminoacetate, ammonium phosphate, calcium phosphate, calcium hydroxide, magaldrate. Preferably, the polymer comprises from 50% to 100% lactide or lactic acid, which may be a D isomer, L-isomer, or a D-,L-racemic mixture, and from 50% to 0% of a glycolide or glycolic acid. The polymer has an inherent viscosity of from 0.1 to 2.0 dl/g.

The polymer solution comprises from 0.1 to 20% of the biologically active agent or a composition comprising the biologically active agent and a carrier. In those instances where the amount of biologically active agent incorporated into the polymer solution is sufficient to promote formation of an interconnected network of pores, addition of carrier to the polymer solution is optional. In those cases where the amount of bioligically active agent incorporated into the polymer solution is low (e.g., due to cost, toxicity, etc.), it is preferred that a carrier be added. Examples of suitable carriers are albumin, gum arabic, gelatin, dextran, a water soluble amino acid, a monosaccharide, a disaccharide, and combinations thereof.

The polymer solution comprises from 0.5 to 20% of the basic additive. In those cases where the amount of basic additive dispersed in the solution is low, i.e. from 0.5% to 3% w/w, it is preferred that the porosity of the polymeric delivery system be increased. Methods for increasing the porosity include adding a pore-forming agent to the polymer solution, increasing the amount of biologically active agent or the composition comprising the biologically active agent and carrier to a value of 5 to 20% (w/w), or using a low concentration of polymer, e.g. 40–300 mg/ml of polymer in the organic solvent. In those cases where the polymer concentration is high, e.g. 1200 mg/ml or the inherent viscosity is high, it is preferred that the polymer solution comprise from 3 to 20% by weight of the basic additive.

Another method of preparing biodegradable polmeric delivery systems for stabilizing the biologically active agents encapsulated therein involves blending a pore-forming agent with a polymer which comprises from 50% to 100% lactide or lactic acid and from 50% to 0% glycolide or glycolic acid. Examples of suitable pore-forming agents are polyethylene glycol (PEG) and water soluble poloxamers. Preferably, the pore-forming agent has a molecular weight of from 500 to 30,000, more preferably from 4000 to 10,000.

The methods of the present invention are suitable for preparing large delivery systems having a weight average diameter of 5 to 500 mm, intermediate-sized delivery systems having a weight average diameter of 100 to 5000 $\mu$m, and small delivery systems having a weight average diameter of from 10 nm to 100 $\mu$m. The delivery systems of the present invention encompass spheres, including microspheres and nanospheres, cylinders, including millicylinders, and particles.

When aqueous soluble compounds are encapsulated in PLGA delivery systems, they are typically distributed throughout the polymer. However, for many processes that are used to prepare PLGA delivery systems, there is a large difference in content of the encapsulated compound at the surface of the polymer relative to the bulk. This phenomenon, the presence of acidic impurities in the polymer, and erosion events (e.g., water uptake, acid-catalyzed polyester hydrolysis, sequestration of low-molecular-weight acids, polymer permeability changes, pH-gradients, polymer glass transition changes, etc.) often result in a lowering of microclimate pH in PLGAs.

Controlled-release systems for proteins and peptides using poly(lactide-co-glycolide) (PLGA) have been studied for more than one decade. Although this type of biodegradable polymer has been successful in delivery of small peptides such as LHRH analogues, the delivery of large globular proteins in PLGA has been limited because of the irreversible inactivation of these therapeutic agents prior to their release in vivo. Previous work from our group has shown that encapsulated bovine serum albumin (BSA) in PLGA systems forms insoluble non-covalent aggregates and is hydrolyzed after incubation in a physiological buffer at 37° C. for 28 days. The acidic pH and intermediate water content existing in the polymer were implicated as two major factors causing instability of the encapsulated protein, and the BSA was stabilized by co-encapsulating poorly water-soluble basic inorganic salts such as $Mg(OH)_2$ The incorporation of the basic additive in the formulation was also successful in stabilizing therapeutic proteins such as recombinant human basic fibroblast growth factor and bone morphogenetic protein-2.

In this study, to further characterize the stabilization mechanism by co-encapsulation of $Mg(OH)_2$, the effect of basic additive type and content on protein stability and release kinetics in PLGA delivery devices was studied. Since acid-induced inactivation pathways (e.g., at pH<3) are common for most proteins, BSA was selected as a model protein. BSA undergoes unfolding from its F to E form at pH 2.7, and forms non-covalent aggregates in PLGA presumably due to this unfolding. The influence of $Mg(OH)_2$ on the delivery system such as pH change in the release medium, polymer degradation and water uptake kinetics was also examined. In addition, the basicity of the salt as well as the loading of base and protein were examined for their effects on BSA aggregation.

Our results confirm that below a critical loading of either basic salt or protein, both acidic and neutral pH regions in the polymer are present. Successful neutralization by the salt requires selection of the appropriate base as well as the appropriate combination of base and protein loading, which allows the base to diffuse to all the protein-containing pores and neutralize all the acidic regions in the polymer.

Materials and Methods

Chemicals

Poly(DL-lactide-co-glycolide) 50/50 with inherent viscosity of 0.23, 0.41, and 0.63 dl/g in hexafluoroisopropanol were purchased from Birmingham Polymers, Inc. (Birmingham, Ala.). Bovine serum albumin (A-3059, Lot 32H0463) was purchased from Sigma Chemical Co. (St. Louis, Mo.). Poly(vinyl alcohol) (80% hydrolyzed with Mw range of 8,000–9,000), $Mg(OH)_2$, $Ca(OH)_2$, and $Ca_3(PO_4)_2$ were obtained from Aldrich Chemical Co. (Milwaukee, Wis.). $ZnCO_3$ was from ICN Biopharmaceuticals Inc. (Aurora, Ohio). All these salts were fine powders (<5 $\mu$m) and were used as received.

Preparation of PLGA Cylindrical Implants

A solvent extrusion method similar to that used previously by our group for intraocular implants was used to prepare the PLGA cylinders with a diameter on the millimeter scale, which we term millicylinders. Briefly, a uniform suspension of sieved protein powder (<90 $\mu$m) with or without basic salt in 50% (w/w) acetone-PLGA 50/50 solution was loaded in a syringe and extruded into a silicone tubing (I.D. 0.8 mm) at about 0.1 ml/min. The solvent extruded suspension was dried at room temperature for 24 h and then dried in a vacuum oven at 45° C. for another 24 h before testing. The protein loading was calculated as the percentage of amount of BSA versus the total weight of mixture (i.e., protein, polymer, and salt).

Evaluation of BSA Release From PLGA Implants

Release of protein was carried out in PBST (which consists of PBS (7.74 mM $Na_2HPO_4$, 2.26 mM $NaH_2O_4$, 137 mM NaCl, and 3 mM KCl, pH 7.4), and 0.02% w/v Tween® 80) at 37° C. under perfect sink conditions. Millicylinders (10×0.8 mm, 5–10 mg or microspheres (about 20 mg) were placed in I ml of the release medium and the medium was replaced at each time point. The protein content was determined by using Coomassie plus protein assay reagent, which is also compatible with denaturing agents (e.g., 6 M urea) and reducing agents (e.g., 10 mM DTT).

Evaluation of BSA Stability Within PLGA Implants

Protein stability was assessed by the percentage of water insoluble non-covalent BSA aggregates generated within the implants versus the initial encapsulated protein. Protein stability within PLGA implants was analyzed as follows: First, millicylinders with a length of 1 cm were incubated under 80% and 96% relative humidity (RH) at 37° C. for 21 days. Then, the polymer was dissolved in acetone and centrifuged to spin down the protein. The remaining protein pellet was washed three times with acetone and then air-dried. The final protein pellet was analyzed as in *Analysis of the Protein Extracted from PLGA Implants*. The protein remaining in PLGA implants after release in PBST at 37° C. for 28 days was also extracted similarly and analyzed as above.

Analysis of the Protein Extracted From PLGA Implants

The BSA pellet extracted from PLGA implants was first reconstituted in PBST and incubated at 37° C. overnight to determine the soluble protein fraction remaining in the polymer. Any remaining aggregates were collected by centrifugation again, and brought up in the denaturing solvent (PBST/6 M urea/1 mM EDTA) and incubated at 37° C. for 30 mm to dissolve non-covalent bonded BSA aggregates. Then, any final undissolved BSA aggregates were collected again and dissolved in the reducing solvent (the denaturing solvent plus 10 mM DTT) to dissolve any disulfide-bonded aggregates.

Protein Assay

For quantitation of soluble BSA, a modified Bradford assay was used as follows: 10 $\mu$l of standard or sample in PBST was added to 250 $\mu$l of Coomassie reagent/well on a 96-well plate and then the plate was read at 595 nm using a Dynex MRX microplate reader (Dynex Technology, Inc., Chantilly, Va.). The concentration range of the standard curve was 50 to 1000 μg/ml. For quantitation of non-covalent and covalent BSA aggregates, the solvents used for preparation of standards and samples were 6 M urea and 6 M urea/10 mM DTT, respectively.

Measurement of Water Uptake in PLGA Millicylinders

After incubation either in PBST or under relative humidity at 37° C., the millicylinders were blotted with tissue paper and weighed immediately. They were then freeze-dried. The water uptake of millicylinders was calculated by:

Water uptake $(\%)=(W_1-W_2)/W_2 \times 100\%$

Where $W_1$ and $W_2$ are the weights of the fully hydrated millicylinders and the dried millicylinders, respectively.

Measurement of Molecular Weight of PLGA

Weight-averaged molecular weight ($M_w$) of the degraded polymers was measured by gel permeation chromatography (GPQ on a Styragel™ HR 5E column (7.8×300 mm, Waters, Milford, Mass.), which was performed on a HPLC system (Waters, Milford, Mass.) equipped with a refractive index detector (Hewlett Packard). The mobile phase was tetrahydrofuran with a flow rate of 1 ml/min. Mw was calculated based on polystyrene standards (Polysciences Inc., PA) using Millenium Software Version 2.10.

SEM Image Analysis of PLGA Implants

Images of PLGA millicylinders were obtained by using a Philips XL30 field emission gun scanning electron microscope (SEM). Samples were coated with conductive-old palladium prior to the analysis.

pH Measurement of Saturated Basic Salts in Water

Basic salts (i.e., $Mg(OH)_2$, $Ca(OH)_2$, $ZnCO_3$ and $Ca_3(PO_4)_2$) in excess of their solubility were added to 5 ml of distilled water. The suspension was then incubated at 37° C. for 7 days. The pH of the supernatant was determined with a Corning 430 pH meter (Corning Inc., NY).

EXAMPLES

The following examples are for purposes of illustration only and are not intended to limit the scope of the claims which are appended hereto.

Example 1

Effect of $Mg(OH)_2$ and Protein Loading on Stability in Millicylinders

Earlier work demonstrated that after an initial burst on the first day, BSA release from 15% BSA/millicylinders (0.63 dl/g PLGA 50/50) during 4 weeks incubation in PBST at 37° C. is insignificant, and the remaining protein mostly becomes water-insoluble non-covalent aggregates. It has been shown that the BSA aggregation is mainly caused by acidic microclimate pH generated by polymer degradation and water uptake by the polymer during incubation in PBST. It has also been found that incorporation of 3% $Mg(OH)_2$ into 15% BSA/PLGA50/50 millicylinders can increase BSA release from PLGA cylindrical implants and reduce BSA aggregation. Structural characterizations by using SDS-PAGE, JEF, CD, and fluorescence spectroscopy have confirmed that the structure of BSA from 3% $Mg(OH)_2/15\%$ BSA devices is mostly retained in a native form.

To examine the effect of $Mg(OH)_2$ content, the base was co-encapsulated in 15% BSA/PLGA millicylinders as a function of base loading and the BSA release. The study was carried out in PBST at 37° C. With the increasing $Mg(OH)_2$ content from 0.5% to 6%, both BSA release rate and total releasable amount of protein increased. The residual BSA remaining in these devices after the 4-week release interval was analyzed. In the absence of $Mg(OH)_2$, most of the remaining protein became water insoluble aggregates, which were nearly completely soluble in the denaturing solvent (i.e., non-covalent aggregates were formed). As the content of $Mg(OH)_2$ was increased, the amount of water-insoluble aggregates decreased. As $Mg(OH)_2$ content was raised to 6%, almost no aggregates were formed within the device. For all the aggregates, an insignificant amount of covalent aggregates was observed in each polymer specimen. These results indicate that an increase in $Mg(OH)_2$ content even up to 6% does not generate an alkaline microclimate in the polymer during release.

Stabilization of Encapsulated BSA in PLGA Implants by $Mg(OH)_2$ in the Presence of Moisture The increased release rate of BSA in the presence of $Mg(OH)_2$ brings up a potential artifact when considering BSA stabilization by the salt. If the salt only accelerates release, there may be insufficient time for BSA aggregates to form. To demonstrate the stabilization effect of $Mg(OH)_2$ in the implants with the same amount of encapsulated protein, 15% BSA/PLGA implants with and without 3% $Mg(OH)_2$ were exposed to a humid environment at 37° C., where all the protein remained inside the device during incubation and PLGA degradation occurred due to uptake of water vapor at 37° C. Two different humidities, 80% and 96% RH, were selected since the salt may also affect water content of the protein, which also affects protein aggregation kinetics. After 3 weeks incubation, the remaining BSA was extracted from the polymer.

In the absence of the base, the same type of water-insoluble non-covalent BSA aggregates was observed among the remaining BSA, as previously reported during incubation in the release medium. With the increasing relative humidity, the water content of the device increased and the amount of the aggregates increased. Previous results have shown that more than 60% of the initially encapsulated BSA formed non-covalent aggregates after 2 weeks release in PBST at 37° C. This indicates that during release the microclimate in the polymer may become more acidic due, to the increased water uptake by the polymer. These results further demonstrate that non-covalent BSA aggregation is caused by the acidic microclimate generated from PLGA degradation products.

In contrast, in the presence of 3% $Mg(OH)_2$ much less non-covalent aggregates were generated under both 80% and 96% RH conditions. This result confirms that incorporation of $Mg(OH)_2$ in PLGA implants indeed can inhibit non-covalent BSA aggregation in the absence of protein release. Since the water uptake by the devices with or without the base was similar, the stabilization effect of $Mg(OH)_2$ is most likely through its neutralization of the acidic microclimate pH as the polymer degrades. It has also been found previously that the amount of BSA release from PLGA50/50 (0.64 dl/g) microspheres with or without $Mg(OH)_2$ was almost identical after 28 days release, but the soluble protein remaining in the polymer was significantly greater in the presence of base (i.e., 65% versus 17%). These results confirm the stabilization effect of the base and rule out the potential artifact due to the faster release of the protein in the presence of the salt.

Characterization of Neutralization Effect of $Mg(OH)_2$ in PLGA Implants

To examine the mechanism of how $Mg(OH)_2$ improves BSA stability and enhances release from PLGA, the neutralization effect of $Mg(OH)_2$ in the acidic microclimate of PLGA millicylinders was examined. This effect was confirmed by changes in pH in the release medium and alteration of the PLGA degradation rate. During the release period from day 21 to 28, the pH of 500 µl release medium containing 5 mg, of 15% BSA/PLGA millicylinder dropped to 3.5, while in the presence of 3% Mg(OH)$_2$ the pH was still maintained around 7.0. The characterization of polymer MW by GPC also showed that degradation rate of the polymer in 15%1 BSA/PLGA millicylinders was faster than that in the presence of Mg(OH)$_2$, which suggests that fewer acidic species were generated during release in these Mg(OH)$_2$-containing millicylinders, consistent with the release medium pH data. Therefore, the Mg(OH)$_2$ inhibits the autocatalytic degradation mechanism of PLGA. These results show that Mg(OH)$_2$ indeed neutralized the acidic microclimate, which is consistent with the result reported by our group previously using a fluorescent probe. Thus, it is concluded that Mg(OH)$_2$ stabilizes the encapsulated BSA through neutralizing acidic species generated from PLGA degradation.

To explain the faster release profiles in the presence of Mg(OH)$_2$, the water uptake kinetics of the millicylinders was characterized. The presence of 3% Mg(OH)$_2$ significantly increased the water uptake rate of PLGA millicylinders. At 7 days, the total water content in 3% Mg(OH)$_2$/15% BSA/PLGA millicylinders was much higher than the polymer without Mg(OH)$_2$. This result suggests that the higher permeability is expected in the millicylinders with Mg(OH)$_2$.

The reason that Mg(OH)$_2$ increases water uptake is likely due to changes in water activity within the PLGA millicylinders. Mg(OH)$_2$ increases the microclimate pH in the polymer, which will cause the dissociation of the end groups (i.e., —COOH) with a p$K_a$ of 3.83 for both glycolic- and lactic acids of PLGA and ionization of the monomers/oligomers. Therefore, ionization of the polymer end groups and the increased osmotic pressure will be the driving force for water molecules to diffuse into the polymer matrix, resulting in higher water content.

Effect of Protein Loading on BSA Release and Stability

Confocal micrographs of fluorescein-loaded PLGA microspheres with coencapsulated Mg(OH)$_2$ and no protein, indicate a population of both acidic and neutral pH pores in the polymer matrix. This pH heterogeneity suggests that in order for BSA to be stabilized, the base must be able to diffuse to the BSA-containing pores. Moreover, from control studies we have observed that 15% protein loading is sufficient for BSA to percolate effectively throughout the polymer. For example, if the BSA loading without the base is increased to 20%, >90% of the protein is release in 1 day. Therefore, a decrease in the percolation of BSA particles in the polymer with basic salt would be expected to cause a rise in BSA aggregation, corresponding to increased exposure of BSA to acidic pores.

To test this hypothesis, BSA loading was decreased to reduce its percolation, and the BSA release was studied. As expected, as the loading was decreased. an increase in BSA aggregation was observed. As BSA loading was decreased there was also a corresponding decrease in the release rate. A similar phenomenon was observed for the stabilization of BSA in PLGA50/50 microspheres at a similar BSA loading (4%) to the 5% BSA/PLGA millicylinders.

Example 2

Effect of MgCO$_3$ on Protein Stability in PLGA Millicylinders

A higher soluble base, MgCO$_3$, stabilized BSA much better than the Mg(OH)$_2$, even though both bases neutralize acidity in a saturated solution to the same extent.

Example 3

Effect of ZnCO$_3$ and Ca(PO$_4$)$_2$ and Ca(OH)$_2$ on Protein Stability in PLGA Millicylinders To examine the effect of the basic salts with different alkalinity on the stability and release of BSA encapsulated in the polymer, one relatively strong basic salt, Ca(OH)$_2$, was chosen and two other relatively weak basic salts, ZnCO$_3$ and Ca$_3$(PO$_4$)$_2$, were chosen and examined as to whether similar stability and release profiles could be achieved in 15% BSA/PLGA millicylinders, as was demonstrated with the use of Mg(OH)$_2$ in Example 1 above. The solubilities and pH of these salts are shown in Table 1.

TABLE 2

Effect of basic salts on BSA aggregation in 15% BSA/PLGA (0.63 dl/g) Millicylinders after 2-week release study in PBST at 37° C. (average ± SEM, n = 3)

| Salts | Ca(OH)$_2$ | | ZnCO$_3$ | | Ca$_3$(PO$_4$)$_2$ | |
|---|---|---|---|---|---|---|
| % | 0.5 | 3.0 | 0.5 | 3.0 | 0.5 | 3.0 |
| Soluble BSA[a], % | 51 ± 4 | 13 ± 1 | 36 ± 1 | 30 ± 1 | 44 ± 2 | 52 ± 1 |
| Non-covalent aggregate[b], % | 10 ± 1 | 3.9 ± 0.1 | 30 ± 4 | 10 ± 1 | 30 ± 2 | 8.4 ± 0.3 |
| Covalent aggregate[c], % | n.d.[d] | 11 ± 1 | n.d. | 1.8 ± 0.1 | n.d. | 1.0 ± 0.1 |

[a]Soluble in PBST;
[b]Soluble in PBST containing 6 M urea and 1 mM EDTA;
[c]Soluble in PBST containing 6 M urea, 1 mM EDTA and 10 mM DTT;
[d]n.d. - not detectable With the increasing content of ZnCO$_3$, Ca(OH)$_2$, or Ca$_3$(PO$_4$)$_2$, both the release rate and total releasable amount of BSA increase, which is quite similar to the effect of Mg(OH)$_2$. Analysis of the residual BSA in these devices is discussed next. For ZnCO$_3$ and Ca$_3$(PO$_4$)$_2$, similar to Mg(OH)$_2$, the total amount of water insoluble aggregates decreased with the increasing salt content. For Ca(OH)$_2$, only 0.5% of Ca(OH)$_2$ of the loading was required to attain a similar inhibition of BSA aggregation as attained with 3% of the weak bases. However, when the loading was raised to 3%, a significant amount of covalent bonded aggregates of BSA formed, which suggests that the microclimate pH in the presence of Ca(OH)$_2$ becomes more alkaline than with the weakly basic salts. Compared to a pH of 9.97 for saturated Mg(OH)$_2$ solution, the pH of a saturated Ca(OH)$_2$ solution was found to be 12.4. As pH becomes alkaline, the free thiol group of Cys residues ionizes to become the more reactive thiolate and readily catalyzes disulfide bonded BSA aggregates via thiolate-disulfide interchange. For ZnCO$_3$ and Ca$_3$(PO$_4$)$_2$, the pH of their saturated solution was found to be 7.34 and 7.77, respectively, which indicates that both species are very weak bases. Therefore, compared to Mg(OH)$_2$, after only two weeks incubation, a larger amount of non-covalent aggregates in PLGA millicylinders with ZnCO$_3$ or Ca$_3$(PO$_4$)$_2$ were observed and no detectable amount of covalent aggregates were formed (Table 1).

The reason that the BSA release was relatively faster in the presence of ZnCO$_3$ than Ca$_3$(PO$_4$)$_2$ may be explained as follows: Since ZnCO$_3$ will react with protons generated from PLGA degradation to form a weak acid H$_2$CO$_3$ (p$Ka_i$= 6.35 [14]), and while for Ca$_3$(PO$_4$)$_2$ a strong acid H$_3$PO$_4$ (p$Ka_i$=2.16 [14]) will be produced, it is expected that the microclimate in the millicylinders with Ca$_3$(PO$_4$)$_2$ will be more acidic than that with $ZnCO_3$. This was confirmed by the following experimental data simulating the reaction of acidic species and basic: salt occurring in the polymer: when 100 μl of 1 N HCl was added to a saturated $ZnCO_3$ solution containing excess of salt, the pH dropped to 5.36, whereas the same amount of HCl added to a saturated $Ca_3(PO_4)_2$ solution caused the pH to drop to 3.71. The difference of the neutralization effect from the salts is also reflected in the different water contents of their PLGA devices. The 3% $ZnCO_3$/15% BSA/PLGA millicylinders had a water content of 168±5% (n=3) after 2-week release compared to 81±1% (n=3) in the 3% $Ca_3(PO_4)_2$/15% BSA/PLGA millicylinders. which suggests that $ZnCO_3$ should raise the microclimate pH in the polymer greater than does $Ca_3(PO_4)_2$. These results show that the homogeneity of the microclimate pH inside PLGA implants can be controlled by selecting certain types of basic salts, which suggests a potential approach to optimize the stability of encapsulated pharmaceuticals in PLGA including, therapeutic proteins.

Overall, as seen in this study, although adding certain percentage of basic salts to BSA/PLGA devices can reduce the aggregation and enhance the release, higher content of salts results in shorter release duration while lower content of salts cannot eliminate aggregation. Therefore, it may desirable to add other excipients, such as sucrose to the delivery systems which contain high levels of salts in order to increase release duration. In a recent study, we found that encapsulation of sucrose into 15% BSA/3% $Mg(OH)_2$/PLGA can also minimize the amount of aggregates formed during release but slow down the release rate.

Example 4

Investigation of Protein Release and Stability in PLGA Microspheres

The purpose of the work in this example is to 1) investigate the protein release and stability in PLGA microspheres (which are prepared by the methods different from cylindrical implants and have smaller geometry; i.e., 10–100 μm), and 2) test whether the stabilization approach developed for the cylindrical implants was applicable for protein delivery from this more challenging PLGA system. To achieve these objectives, BSA was chosen as a model protein and its release and stability was studied in PLGA microspheres. First, the standard water-in-oil-in-water (W/O/W) double emulsion and solvent evaporation method was used to encapsulate BSA into PLGA microspheres. As expected, the same BSA aggregation mechanism and incomplete release characteristics were observed during in vitro release as for the cylindrical implants. When basic salts (e.g. $ZnCO_3$, $Mg(OH)_2$, and $MgCO_3$) were co-encapsulated into the microspheres made of high MW PLGA50/50 (0.64 dl/g), the BSA aggregation rate was reduced but no significant amount of protein was released over one month. However, continuous protein release was achieved when the microspheres were prepared from low MW polymer (0.20 dl/g) in the presence of basic salts. In addition, protein release and stability in PLGA microspheres prepared by an oil-in-oil (O/O) emulsion encapsulation method were also studied. It was also observed that in the presence of basic salts (e.g., $Mg(OH)_2$ and $ZnCO_3$), continuous protein release from O/O microspheres was achieved and less encapsulated protein became aggregates compared to without basic salts. This study further confirms the effectiveness of utilizing basic salts to stabilize the encapsulated proteins and to control their release from PLGA microspheres.

Poly(d,1-lactide-co-glycolide) (PLGA) and poly(d,1-lactide) (PLA) polymers were purchased from Birmingham Polymers, Inc. (Birmingham, Ala.). PLGA50/50 polymers with inherent viscosity of 0.20, 0.64 and 0.70 dl/g were used, and PLGA75/25, PLGA85/15 and PLA had inherent viscosity of 0.58, 0.66 and 0.69 dl/g, repectively. Bovine serum albumin (A-3059, Lot 32H0463), Span 85 surfactant, and cotton seed oil were from Sigma Chemical Co. (St. Louis, Mo.). Petroleum ether with 50–110° C. boiling range was obtained from J. T. Baker (Phillipsburg, N.J.). Actonitrile and acetone (analytical grade) were from Fisher Scientific Co. (Pittsburgh, Pa.). Poly(vinyl alcohol) (PVA) and fine $Mg(OH)_2$ powder (<5 μm) were from Aldrich Chemical Co. (Milwaukee, Wis.) and $ZnCO_3$ powder was from ICN Pharmaceuticals Inc. (Auroroa, Ohio). All other chemicals were of analytical grade or purer and purchased from commercial suppliers.

For preparation of PLGA50/50 (0.64 dl/g) microspheres, 100 μl of BSA solution (150 mg/ml or 300 mg/ml) in 10 mM phosphate buffer (pH 7.4) was first added to 1 ml of 30% w/v PLGA-$CH_2$—$CL_2$ solution with or without basic salts. Then, the mixture was homogenized at 10,000 rpm using a homogenizer (Model $IQ^2$, VirTis Co., Gardiner, N.Y.) for 1 min in an ice bath. The formed W/O emulsion was immediately added to 1 ml of 2% w/v polyvinyl alcohol (PVA) aqueous solution and the mixture was vortexed for 20 s to form a W/O/W emulsion. The double emulsion was immediately transferred to 100 ml of 0.5% w/v PVA aqueous solution under stirring at a constant rate. The microspheres were stirred continuously for 3 h at room temperature. The hardened microspheres were collected by centrifugation and washed with ice-cold water 3 times. Finally, the microspheres were lyophilized for 24 h to get the final dry product with a Labcono FreeZone® 6 Liter Freeze Dry System (Kansas City, Mo.).

For preparation of PLGA 50/50 (0.20 dl/g) microspheres, all the materials and procedures were the same except that 70% w/v polymer concentration was used instead of 30%.

To prepare PLGA microspheres by the oil-in-oil (O/O) emulsion method/solvent extraction method, BSA particles (directly ground from the lyophilized powder and sieved to <45 μm) were added to a polymer solution in 1 ml of facetonitrile. The suspension was homogenized at 15,000 rpm with a homogenizer (Model $IQ^2$, Virtis Co., Gardiner, N.Y.) for 3 min on an ice bath, and then slowly was added dropwise to a 100 ml of cotton seed oil (Sigma Chemical Co.) containing 1.6 grams of Span 85 under stirring at 700 rpm. The formed O/O emulsion was continued to stir under ambient conditions for 5 hr. Thereafter, 100 ml of petroleum ether was added and stirring was continued for another 15 min. The microspheres were then collected by filtration through a 0.45 μm membrane filter (Gelman Sciences) and then lyophilized at room temperature for 2 days.

To prepare BSA/PLGA microspheres by the W/O/W emulusion method, to reduce the burst effect, generally the volume ratio of the internal phase (protein solution) to the external phase (polymer solution) should be below 1/10 and higher polymer concentration should be used [Cleland 1997]. Therefore, in this study, the ratio of 1/10 and the PLGA50/50 (0.64 dl/g) concentration of 300 mg/ml (700 mg/ml was used for PLGA50/50 (0.20 dl/g)) for all the preparations, which resulted in high encapsulation efficiency for these preparations (i.e., >80%). By SEM, PLGA microspheres prepared by this method appeared mostly spherical with very smooth surfaces and their size range was between 60 and 70 μm.

The in vitro release and stability of BSA encapsulated in W/O/W PLGA microspheres was examined. More specifically, the in vitro release profiles of 4% and 8% BSA loaded PlGA50/50 (0.64 dl/g) microspheres from the W/O/W preparations were studied. The burst effect increased with the BSA loading likely due to more percolation protein clusters formed across the microsphere diameter. However, over the 28-day release, both 4% and 8% BSA preparations did not release significant amount of protein from the polymer after the first day initial burst. This incomplete release phenomenon is quite similar to results published in the literature.

At the end of release study, after removing the polymer with acetone, the remaining BSA in the polymer was also found to be partially insoluble in PBST buffer (Table 2). However, all these aggregates were soluble in 6 M urea, which indicates that encapsulated BSA also formed non-covalent aggregates during release from PlGA microspheres. This result shows that formation of non-covalent BSA aggregates is a common phenomenon in both PLGA millicylinders and microspheres, which suggests that the microclimate in the PLGA microspheres during release may also become very acidic and could be equivalent to the pH in the PLGA millicylinders (pH<3).

TABLE 3

Aggregation of encapsulated BSA in PLGA50/50 (0.64 dl/g) microspheres over 28-day release in PBST at 37° C. (Average ± SEM, n = 3)

| BSA loading, % | Released, % | Soluble residue, % | Insoluble residue, % |
| --- | --- | --- | --- |
| 4 | 4.4 ± 0.1 | 17 ± 2 | 68 ± 6 |
| 8 | 23 ± 1 | 45 ± 1 | 25 ± 3 |

The incomplete release and non-covalent BSA aggregation also occurred in the PLGA50/50 microspheres made of lower MW polymer (0.20 dl/g). No significant amount of protein was released from 3% BSA/PLGA50/50 (0.20 dl/g) microspheres over 51 days release, and the remaining BSA mostly became water-insoluble non-covalent aggregates. This result indicates that non-covalent aggregation of encapsulated BSA in PLGA is a common instability pathway no matter whether high MW or low MW polymer is used.

The effect of basic salts on BSA release and stability in W/O/W microspheres was studied. Since non-covalent aggregation of encapsulated BSA indicates existence of the acidic microclimate in the PLGA microspheres during release, to examine whether basic salts such as $Mg(OH)_2$ could also be used to inhibit BSA aggregation in PLGA microspheres, $Mg(OH)_2$ was co-encapsulated into 4% BSA/PLGA50/50 (0.64 dl/g) microspheres. The in vitro release and stability over 28-day release in PBST medium at 37° C. were studied. The cumulative BSA release over 28 days did not increase significantly with $Mg(OH)_2$ content, which is different from that of PLGA millicylinders. However, the BSA aggregates in the remaining protein from the polymer decrease significantly with increasing $Mg(OH)_2$ content from 0.5% to 3%, which confirms that non-covalent BSA aggregation can also be inhibited by neutralizing the acidic microclimate in PLGA microspheres with $Mg(OH)_2$.

In most protein delivery applications, continuous release profiles form PLGA microspheres are desirable. To examine whether increasing BSA loading can achieve continuous release in the presence of 3% $Mg(OH)_2$, 8% BSA loaded PLGA microsphere were prepared. Their in vitro release profiles were studied. Similar to that in the absence of $Mg(OH)_2$, increasing BSA loading only increased the initial burst but did not achieve continuous release effect in the presence to 3% $Mg(OH)_2$.

To compare the effect of other basic salts on the release and stability of BSA encapsulated in PLGA microspheres by the W/O/W emulsion preparation, $MgCO_3$, $ZnCO_3$, and $CaCO_3$ were co-encapsulated into 4% BSA/PLGA50/50 (0.64 dl/g) microspheres. Their in vitro release profiles were studied. Here, $MgCO_3$ allowed BSA to continuously release up to 10% over 28 days and all other basic salts did not significantly increase the release of BSA from PLGA microspheres (<5%) after the first day burst. This may be caused by higher water uptake in the presence of $MgCO_3$ due to its higher solubility. Upon 28 days release, the remaining BSA was extracted and the aggregation results were noted. As expected, compared to that without basic salts (Table 3), all the basic salts increased the soluble residue and reduced the insoluble residue. Due to the more alkaline property of $Mg(OH)_2$ and $MgCO_3$, the incorporation of these salts increased the soluble BSA residue more compared to the weaker bases ($CaCO_3$ or $ZnCO_3$), which further confirmed the neutralization effect of basic salts on the stability of encapsulated BSA in PLGA microspheres.

TABLE 5

Effect of basic salts on BSA aggregation in W/O/W 4% BSA/PLGA 50/50 (0.64 dl/g) microspheres over 28-day release in PBST at 37° C. (Average ± SEM, n = 3)

| Basic salts | Released, % | Soluble residue, % | Insoluble residue, % |
| --- | --- | --- | --- |
| 3% $CaCO_3$ | 10 ± 1 | 33 ± 1 | 42 ± 1 |
| 3% $ZnCO_3$ | 9.8 ± 0.1 | 46 ± 1 | 33 ± 1 |
| 3% $Mg(OH)_2$ | 6.9 ± 0.2 | 65 ± 2 | 26 ± 1 |
| 3% $MgCO_3$ | 17 ± 2 | 59 ± 1 | 13 ± 2 |

Although the incorporation of the basic salts indeed inhibited the protein aggregation, it did not significantly increase the protein release from microspheres made of high MW polymer (0.64 dl/g). To examine whether these basic salts can increase protein release from microspheres made of lower MW polymer, they were co-encapsulated into 3% BSA/PLGA50/50 (i.v.=0.20 dl/g) microspheres. The release profiles were studied. In the absence of basic salts, a very small amount of encapsulated BSA was released over 51 days. In contrast, in the presence of 3% $Mg(OH)_2$, $ZnCO_3$, or $Mg(OH)_2$, the BSA release rate increased, especially for 3% $MgCO_3$. Therefore, for the microspheres with lower MW PLGA, co-encapsulation of basic salts can lead to continuous protein release from the polymer. This may result from higher permeability of the lower MW polymer matrix due to its more hydrophilicity and lower glass transition temperature. At the end of the release study, the composition of the remaining BSA in the microspheres was analyzed and listed in Table 4. Without basic salts, the total detectable BSA amount was below 50% of initially encapsulated protein based on the pre-determined BSA loading, which may be caused by extensive protein hydrolysis due to exposure to acidic microclimate for 51 days. The co-encapsulated basic salts actually increased the detectable amount of BSA although a significant amount of non-covalent aggregates were also generated even in the presence of 3% $Mg(OH)_2$.

TABLE 6

Effect of basic salts on BSA aggregation in 3% BSA/PLGA50/50
(0.20 dl/g) microspheres over 51-day release in PBST at
37° C. (Average ± SEM, n = 3)

| Basic salts | Released, % | Soluble residue, % | Insoluble residue, % |
|---|---|---|---|
| No salts | 16 ± 2 | 0.9 ± 0.1 | 24 ± 3 |
| 3% $ZnCO_3$ | 41 ± 1 | 0.5 ± 0.1 | 22 ± 1 |
| 3% $Mg(OH)_2$ | 37 ± 2 | 2.1 ± 0.1 | 30 ± 2 |
| 3% $MgCO_3$ | 68 ± 2 | 24 ± 1 | 1.5 ± 0.2 |

To understand how each basic salt affected BSA aggregation in the lower MW PLGA microspheres, the pH changes in the release medium were examined. $ZnCO_3$ did not show any obvious neutralization effect. The fact that $ZnCO_3$ increased BSA release may be due to: 1) ionized polymer end groups (—COOH) caused by localized pH neutralization, 2) enhanced water uptake due to the formation of soluble $Zn^{2+}$ and $HCO_3^-$ ions in the acidic pH. In the presence of 3% $Mg(OH)_2$ or $MgCO_3$, initially the pH of the release medium was higher than without basic salts. However, after 35 days, the pH also became acidic (<4.5) even in the presence of $Mg(OH)_2$, which may be due to the depletion of the basic salts caused by extensive polymer erosion. In the case of $MgCO_3$, due to its higher solubility in water than $Mg(OH)_2$, more than 50% of initially encapsulated BSA was released, so the polymer matrix should be more permeable to many acidic polymer degradation products, which is expected to have less acidic microclimate and result in fewer BSA aggregates. While in the case of $Mg(OH)_2$, most of the protein still remained in the polymer end and therefore, the microspheres should have a lower permeability. After the base polymer is depleted, the acidic species will be accumulated, which causes aggregation. Therefore, selection of specific basic salt type and content is critical to pH control, which appears to be necessary for stabilization and controlled release of proteins encapsulated in PLGA systems.

Example 5

Preparation and Study of BSA/PLGA Microspheres Prepared by O/O Emulsion Method

Encapsulated BSA formed non-covalent aggregates in W/O/W PLGA microspheres during release, which can be inhibited by co-encapsulation of basic salts such as $Mg(OH)_2$ and $MgCO_3$. To test whether the stability of encapsulated BSA in PLGA microspheres during relesase is encapsulation method dependent, BSA was encapsulated into PLGA microspheres by another commonly used anhydrous encapsulation method—the oil-in-oil emulsion/solvent extraction method. For O/O preparations, a severe burst effect and poor emulsion stability were two major problems. In order to solve these problems, several formulation variables may be controlled, including polymer composition (lactide/glycolide ratio), polymer concentration, and protein loading. Therefore, the first objective of this study was to prepare spherical PLGA microspheres with a low burst effect by adjusting these variables.

The effect of polymer lactide/glycolide ratio on preparation and initial burst of these microspheres was studied. Since it is known that PLGA microspheres made of higher MW polymer have lower burst effect, a series of PLGA polymers with similar inherent viscosity (0.58–0.70 dl/g) but different lactide/glycolide (LA/GA) ratio (50/50, 75/25, 85/15 and 100/0) were chosen. Using a polymer concentration of 300 mg/ml, 5% loaded BSA microspheres were prepared. In all the preparations, the emulsion was very stable and could be observed in the SEM. All these preparations resulted in very spherical microspheres with smooth surfaces. Most of the microspheres have the average size range from 80 to 100 μm. Also this preparation method has a very high encapsulation efficiency (>94%).

The effect of polymer concentration on preparation and initial burst was studied. In O/O emulsion preparations, low polymer concentrations (below 100 mg/ml) were usually used in order to form spherical microspheres. To examine how the polymer concentration affects the emulsion in this preparation method, 100, 200, 300, 400 mg/ml of PLGA85/15 (0.66) were tested in the presence of 5% BSA particles. For polymer concentrations from 100 to 300 mg/ml, the emulsions were very easily formed and spherical particles with smooth surfaces were obtained. The average size of microspheres increased from 63 to 93 μm with increasing polymer concentration from 100 to 300 mg/ml. In this polymer concentration range, all the preparations had very high encapsulation efficiency (>91%; Table 5). For 40 0 mg/ml, however, the emulsion could not be formed because the polymer solution was too viscous.

TABLE 6

Effect of polymer concentration on preparations of 5% BSA/PLGA85/15
(0.66 dl/g) microspheres and the initial burst.

| Polymer Conc. (mg/ml) | Size (μm)[a] | BSA loading (%)[b] | Enapsulation efficiency (%)[c] | 1st day release (%)[b] |
|---|---|---|---|---|
| 100 | 63 ± 15 | 4.56 ± 0.22 | 91 | 68 ± 1 |
| 200 | 79 ± 30 | 4.76 ± 0.11 | 95 | 48 ± 1 |
| 300 | 92 ± 22 | 4.80 ± 0.03 | 96 | 22 ± 1 |

[a]average ± SD, n = 50;
[b]average ± SEM, n = 3;
[c]encapsulation efficiency = measured loading/calculated loading × 100%.

No obvious protein particles were found on the surface, which indicates most of the protein particles were encapsulated into the microspheres. However, the burst effect increased dramatically with decreasing the polymer concentration, which may be caused by more porous structure of PLGA microspheres with low polymer concentration.

To test the effect of BSA loading on preparation of PLGA microspheres, 5, 10, 15% BSA loaded PLGA85/15 microspheres were prepared at a polymer concentration of 300 mg/ml. It was found that most microspheres were very spherical and had very smooth surfaces. No observable protein particles were absorbed on the surface, which indicates that most protein was encapsulated into the polymer. All the preparations also showed high encapsulation efficiency (>90%; Table 6). As expected, with the increasing BSA loading the initial burst increases, due to the formation of more percolation clusters of protein particles across the microsphere diameter.

TABLE 6

Effect of BSA loading on preparations of PLGA85/15 (0.66 dl/g)
microspheres and the initial burst.

| BSA loading (%) | Size (μm)[a] | BSA loading (%)[b] | Enapsulation efficiency (%)[c] | 1st day release (%)[b] |
|---|---|---|---|---|
| 5 | 92 ± 22 | 4.80 ± 0.03 | 96 | 22 ± 1 |
| 10 | 94 ± 27 | 9.59 ± 0.21 | 96 | 46 ± 1 |
| 15 | 102 ± 30 | 13.5 ± 0.12 | 90 | 67 ± 2 |

[a]average ± SD, n = 50;
[b]average ± SEM, n = 3;
[c]encapsulation efficiency = measured loading/calculated loading × 100%.

The effect of formulation variables on BSA release and stability in O/O microspheres was studied. To test whether continuous protein release is achievable by adjusting the formulation variables by the O/O emulsion method, the in vitro release kinetics of microspheres prepared from PLGA was examined as a function of LA/GA ratio, polymer concentration, and protein loading. The results showed that, over the 35-day release, except for PLGA50/50, all these formulations released less than 10% protein from microspheres after the first day initial burst, which suggests that continuous protein release was not achievable by simply changing these formulation variables. For PLGA50/50 microspheres, the second burst was likely caused by the known pulse of mass loss from this type of polymer during erosion. The 50:50 LA/GA ratio results in faster polymer degradation compared to the other polymers of lower glycolide content.

At the end of release study, the remaining protein extracted from the polymer was analyzed and the stability noted. The data showed that the LA/GA ratio of PLGA directly affected the stability of encapsulated BSA during release. In the PLGA75/25 and PLA microspheres, very small amount of remaining BSA formed non-covalent aggregates, whereas in the PLGA50/50 microspheres most of remaining protein became water-insoluble aggregates. This result further confirms that the acidic microclimate caused by PLGA degradation is the major source responsible for the formation of non-covalent BSA aggregate during release, because PLGA50/20 degradation rate is faster than other polymers and thereby more acidic species will be generated over 35-day release. This is confirmed by the measurement of pH change in the release medium. For PLGA50/50 microspheres, the pH dropped significantly after 20 days. While for PLGA75/25 and PLA microspheres, the pH still remained at neutral pH over 35 days.

The possible cause for the increased BSA aggregation in PLGA85/15 microspheres relative to PLGA75/25 and PLA is the presence of more low MW species in PLGA85/15. The presence of monomers or oligomers can also produce acidic microclimate even before polymer degradation occurs. This hypothesis was confirmed by the initial pH drop (on day 1 and 4) in the release medium containing PLGA85/15 microspheres, which is likely due to release of these low MW acidic species into the release medium.

The acidic microclimate in the PLGA50/50 microspheres is also shown in the degradation of the remaining soluble protein from the polymer after 35 days incubation in PBST at 37° C. The data showed that the remaining soluble BSA extracted from PLGA75/25, PLGA85/15, and PLA microspheres mostly still retained the same MW as the standard BSA, while the protein from the PLGA50/50 microspheres contained a significant amount of peptide fragments. This result indicates that PLGA50/50 microspheres had a much more acidic microclimate than PLGA75/25, PLGA85/15 or PLA microspheres.

Example 6

Preparation and Study of rhBMP-2/PLGA Microspheres

To prepare the rhBMP-2/PLGA microspheres by the standard water-in-oil-in-water emulsion method, one major difficulty is the low aqueous solubility of rhBMP-2 at neutral pH, which prevents attainment of a high loading of rhBMP-2 in PLGA microspheres. To overcome this problem, the first approach was to add heparin as a polyanion to increase rhBMP-2 solubility at neutral pH. It was found that when the weight ratio of heparin/rhBMP-2 was above 4, rhBMP-2 remained soluble even at 20 mg/ml in water. Therefore a heparin-rhBMP-2 complex (heparin/rhBMP-2 ration 7) was co-encapsulated with BSA into PLGA microspheres. However, the in vitro results showed that significant bleeding was observed surrounding the implants, which indicates that heparin cased hemorrhage. The second approach was to decrease the pH in the buffer to increase rhBMP-2 solubility. Since BSA is not stable at low pH, obviously BSA is not a good candidate as a bulk excipient for rhBMP-2 delivery from PLGA microspheres. Although the salts present in rhBMP-2 lyophilized cake may cause a large burst effect due to their high osmotic pressure, rhBMP-2 has a relatively lower solubility compared to these salts, suggesting that the burst effect may not occur for rhBMP-2. Therefore, 400 $\mu$l of water was directly added to one vial of rhBMP-2 lyophilized cake to prepare a 20 mg/ml rhBMP-2 solution containing a high concentration of salts at pH 4.5. Although rhBMP-2 is a relatively stable growth factor at an acidic pH below room temperature, rhBMP-2 may not survive when exposed to both body temperature and acidic microclimate caused by PLGA degradation (e.g., pH<2). Therefore, based upon previous results, in this formulation 5% $ZnCO_3$ was also added as a neutralizing substance to prevent the generation of extremely low pH in the polymer during release. Meanwhile, $ZnCO_3$ also can increase the polymer water uptake and give protein continuous release from the device.

The SEM images of the microspheres prepared from different polymer concentrations showed that the microspheres from lower polymer concentration were more porous than those prepared from higher polymer concentration. The polymer concentration also affected both the encapsulation efficiency and particle size. With increasing the polymer concentration, both the encapsulation efficiency and average particle size increased (Table 7) which may result from the increased viscosity of the polymer phase.

TABLE 7

Characteristics of rhBMP-2/PLGA50/50 delivery devices.

| | rhBMP-2 loading, %[c] | Encapsulation efficiency, %[d] | Device size |
|---|---|---|---|
| Cylindrical implants | 0.25 ± 0.01 | 83 | o = 0.32 cm, L – 0.4 cm |
| Microspheres (I)[a] | 0.68 ± 0.03 | 68 | 61 ± 14 $\mu$m[e] |
| Microspheres (II)[b] | 0.78 ± 0.02 | 78 | 90 ± 24 $\mu$m |

[a]Prepared from 200 mg/ml polymer concentration;
[b]Prepared from 300 mg/ml polymer concentration;
[c]Average ± SD, n = 2
[d]Encapsulated efficiency = (measured loading)/(theoretical loading) × 100%
[e]Average ± SD, n = 100.

In vitro release kinetics of rhBMP-2 from PLGA devices was characterized. Since rhBMP-2 has very low aqueous solubility and severely absorbs on many surfaces, the released rhBMP-2 in PBST from PLGA may precipitate or absorb on the surface of the container. To minimize the loss of the releases rhBMP-2, the same release medium was used as in the rhbFGF release study for in vitro release, i.e., 1% BSA and 10 $\mu$g/ml of heparin were combined with PBST medium.

The in vitro release profile of rhBMP-2 from PLGA cylindrical implants containing 0.25% rhBMP-2, 15% BSA, and 3% $Mg(OH)_2$ was studied. The data showed that rhBMP-2 did not exhibit a large burst effect compared to rhbFGF or BSA release from 15% BSA/3% $Mg(OH)_2$/PLGA millicylinders, which may be due to lower aqueous solubility of rhBMP-2. Over the 28 days release study, rhBMP-2 was released continuously and slowly from the devices. Since the curve of cumulative rhBMP-2 release percentage versus the square root of release time exhibited a high linearity ($R^2$=0.985), rhBMP-2 release from the cylindrical implants was likely diffusion controlled. At the end of the release study, the remaining rhBMP-2 was extracted and quantified by the BIAcore immunoassay. The total recovery of rhBMP-2 based on the measurement of both cumulative released rhBMP-2 and remaining rhBMP-2 was above 80% (Table 8), which indicates that most of encapsulated rhBMP-2 retained immunoreactivity.

TABLE 8

Recovery of rhBMP-2 form PLGA delivery devices.

|  | Released rhBMP-2 over 28 d, % | Remaining rhBMP-2, % | Recover, %[a] |
|---|---|---|---|
| Cylindrical implants | 55.0 ± 0.5[b] | 25.2 ± 1.0 | 80.2 ± 1.4 |
| Microspheres (I) | 68.7 ± 0.7 | 35.2 ± 1.5 | 104 ± 1.0 |
| Microspheres (II) | 26.5 ± 1.6 | 21.3 ± 1.4 | 47.8 ± 2.7 |

[a]Recovery = total released percentage over 28 d + remaining percentage
[b]Average ± SEM, n = 3

The in vitro release profiles of rhBMP-2 from PLGA microspheres prepared from different polymer concentrations were studied. As expected, the release rate of rhBMP-2 from PLGA microspheres prepared form 200 mg/ml polymer concentration was much faster than that from 300 mg/ml polymer concentration. Both can continuously release immunoreactive rhBMP-2 over 21 days. The big burst effect for Formulation I was likely caused by the very porous structure of these PLGA microspheres. At the end of the release study, the extracted rhBMP-2 from PLGA microspheres was quantified with the BIAcore immunoassay. As shown in Table 8, the full recovery of rhBMP-2 from Formulation I was obtainable while below 50% recovery from Formulation II, which indicated that Formulation I is more stable than Formulation II. The loss of immunoreactive rhBMP-2 in Formulation II may be due to acidic microclimate, because more acidic species are expected to accumulate inside the denser microspheres due to lower permeability.

Example 9

Preparation and Study of tPA/PLGA Microspheres $Mg(OH)_2$ was previously used to neutralized PLGA implants to deliver therapeutic proteins, such as basic fibroblasts factor (bFGF) and bone morphogenetic protein (BMP-2). Here, by using this rationale, tPA was successfully encapsulated into PLGA implants. tPA, a protein with a MW of ~60 K Da is a tissue type endogenous serine proteaese involved in thrombi dissolution. The FDA has approved the use of recombinant tPA in the treatment of myocardial infarction. Controlled release systems for local delivery was developed by using hydrogel to control wound healing. A multi-drug controlled release implant with tPA encapsulated was also tested for the intraocular management of proliferative vitroretinopahty (PVR). Here, 10% tPA powder was encapsulated as received (2% tPA, 75% arginine, 22% phophoric acid, and 1% polysorbate 80) with or without 3% $Mg(OH)_2$ into PLGA millicylinders. Arginine hydrochloride and BSA were added in the release medium to improve the stability of released tPA. The release profile and active residue of tPA after release was evaluated by activity analysis. The data showed that, with $Mg(OH)_2$ encapsulated, the one month release of tPA was increased from 77.1±2.6% to 98.0±0.2% and the recovery (released part+active residue) was increased from 82.7±2.5% to 100.1±1.4% respectively. As far as is known, only very few protein formulations have shown continuous and complete release over one month period without losing activity.

Example 10

Materials and Methods

Reagents.

Poly(DL-lactide-co-glycolide) 50150 with inherent viscosity of 0.20, 0.63, and 0.64 dl/g in hexafluoroisopropanol was from BPI (Birmingham, Ala.). Recombinant human bFGF and BMP-2 were supplied by Scios, Inc. (Mountain View, Calif.) and Orthogene (Fremont, Calif.), respectively. Bovine serum albumin (A-3059, Lot 32HO463) and heparin (H-3393, Lot 86HO454) were from Sigma Chemical Co. (St. Louis, Mo.). Fine $Mg(OH)_2$, $MgCO_3$, and $Ca(OH)_2$ (<5 µm) powders were obtained from Aldrich Chemical Co. (Milwaukee, Wis.). $ZnCO_3$ powder (<5 µm) was from ICN Biomedicals Inc. (Aurora, Ohio). Reagents used in cell culture were from GIBCO BRL products (Life Technologies Inc., Md.). All other chemicals were of analytical grade or purer and purchased from commercial suppliers.

Preparation of PLGA Millicylinders.

A uniform suspension of sieved BSA (<90 4 m) with or without $Mg(OH)_2$ in acetone-PLGA 50/50 (0.63 dl/g) solution (50% w/w) was loaded in a syringe and extruded into silicone tubing (I.D.=0.8 mm) at ~0.1 ml/min (13). The solvent-extruded suspension was dried at room temperature (24 h) and then dried in a vacuum oven at 45° C. (24 h). For preparation of bFGF millicylinders, bFGF was combined with heparin, sucrose and BSA additives at a weight ratio (additive bFGF) of 1, 180, and 1000, respectively, in 0.5 mM EDTA and 10 mM sodium phosphate buffer (pH 7.4). The solution was lyophilized for 2 days at room temperature using a Labconco Freeze Dry System (Kansas City, Mo.) to a fine powder with 4% moisture (determined by a Karl Fisher Titrator (Model DL 18, Mettler-Toledo Inc., NJ)) and sieved before suspension in PLGA-acetone and extrusion. For preparation of BMP-22 millicylinders, solutions of BMP-2 combined with BSA or gum arabic (Sigma, St. Louis, Mo.) were similarly lyophilized and sieved. The millicylinders; were prepared in the same way as for BSA/PLGA millicylinders. All the preparations had a loading efficiency invariably between 85% and 95%. Encapsulated proteins were isolated from the polymer for protein assays according to the Evaluation of BSA Aggregation section.

Preparation of PLGA Microspheres.

BSA was encapsulated into PLGA microspheres similar to a method described by Cohen et al. (14). For preparation of PLGA50/50 (0.64 dl/g) microspheres, 100 µl of 150 mg/ml BSA in 10 mM phosphate buffer (pH 7.4) was added to 1 ml of 30% PLGA-$CH_2Cl_2$ solution with or without basic salts. The mixture was homogenized at 10,000 rpm for 1 min on an ice bath, and then immediately transferred to a 2% polyvinyl alcohol (PVA) aqueous solution. The water-in-oil-in-water emulsion was formed by vortexing the mixture for 20 s. The particles were hardened in 100 ml of 0.5% PVA solution at room temperature for 3 h. The microspheres were collected by centrifugation, washed with water, and then lyophilized to form a dry powder. For PLGA (0.20 dl/g) microspheres, 70% polymer concentration was used. For both formulations, the particles were spherical with an average particle size between 60 and 70 µm (SD=20, N=100) determined with a microscope. The BSA loading was ~4% with an encapsulation efficiency between 70% and 80%.

Evaluation of BSA, bFGF, and BMP-2 Release from the Polymer.

Release of BSA was carried out in phosphate buffered saline/0.02% Tween 80® (PBST). Millicylinders (10×0.8 mm, ~10 mg) or microspheres (~20 mg) were placed in polypropylene tubes containing the release medium (0.5 ml) and incubated at 37° C. under mild agitation. At pre-selected times, the buffer was removed after centrifugation for analysis and replaced with new medium. The protein content in release samples was y determined by using a modified Bradford assay (Coomassie plus protein assay, Pierce, Rockford, Ill.), which is also compatible with the denaturing agents (e.g., 6 M urea) and reducing agents (e.g., 10 mM dithiolthreitol (DTT)) used below. At the end of release the remaining protein content in the devices was determined as described in the next section. The release of bFGF and BMP-2 millicylinders was examined similarly as for BSA except that 1% BSA, 10 µg/ml heparin and 1 mM EDTA were added to the release medium to prevent irreversible inactivation of the protein once released from the polymer.

Evaluation of BSA Aggregation.

PLGA devices were incubated in PBST at 37° C. At pre-selected times, the incubated polymers were removed from PBST (millicylinders) or isolated by centrifugation (microspheres), dried with tissue paper, and dissolved in acetone. After centrifugation and removal of the acetone polymer solution, the remaining BSA pellet was reconstituted in PBST. The BSA solution was then incubated at 37° C. overnight before determining the soluble protein fraction in the polymer; this gave a measure of the water-soluble protein encapsulated (also used for protein loading measurement). Any aggregate was collected by centrifugation and incubated (37° C. for 30 min) in denaturing solvent (PBST/6 M urea/1 mM EDTA); analysis of protein concentration gave the amount of non-covalently bonded BSA aggregates (14). Finally, any remaining undissolved BSA was collected again and dissolved in reducing solvent (10 mM DTT in denaturing solvent) to determine the amount of disulfide-bonded aggregates.

Simulation of BSA Instability in the Polymer Microclimate.

Three experiments were designed to simulate the potential deleterious conditions in PLGA devices. In the pH simulation, BSA (4 mg/ml) in a universal buffer ($H_3PO_4$, HAc and $H_3BO_3$ (40 mM each) titrated with NaOH) was lyophilized from pH 2 to 5 and incubated at 37° C. under 86% relative humidity (R.H.) (15). At various times, the protein was reconstituted in PBST and examined for the type of aggregates as described above. To examine the effect of water, water was directly added to lyophilized BSA at pH 2, sealed and then incubated at 37° C. for 1 week, and analyzed as above (16). To examine protein adsorption, several BSA solutions (1 mg/ml) at pH values from 2 to 7 in the universal buffer were incubated for 1 week at 37° C. with 20 mg of PLGA (0.63 dl/g) microspheres prepared by standard solvent evaporation techniques (17) or 20 mg of fine PLGA powder (0,20 dl/-, <100 µm). Loss of BSA content from solution was used to determine the extent of BSA adsorption to the polymer.

Analysis of Structure and Integrity of Encapsulated BSA.

Fluorescence emission spectra of BSA samples from 300 to 500 nm (240 nm/min) were obtained with a Perkin-Elmer LS50B luminescence spectrometer. Far ultraviolet circular dichroism (CD) spectra (200–250 nm) were recorded with a J-500A Jasco spectropolarimeter (Japan) at room temperature. The integrity of protein samples was determined by both sodium dodecyl sulfate polyacrylamide gel electrophoresis (SDS-PAGE) and isoelectric focusing (IEF) gel electrophoresis, which were performed on a Pharmacia PhastSystem (Pharmacia Biotech.). PhastGel™ gradient 10–15 gels and IEF 3–9 gels (Pharmacia Biotech.) were used for SDS-PAGE and MF analyses, respectively. Coomassie blue staining was performed after separation.

Enzyme-linked Immunosorbent Assay (ELISA) for bFGF.

Immunoreactive bFGF was detected by sandwich ELISA (18, 19). A 96-well plate was coated with monoclonal anti-bFGF (Upstate Biotech. Inc., NY) at 4° C. overnight. Samples or standards of bFGF containing 10 µg/ml heparin and 1% BSA in PBST were added to each well and incubated at 4° C. for 24 h. After washing, polyclonal anti-bFGF (rabbit, Sigma, Mo.) was added (room temperature for 2 h) followed by anti-rabbit IgG-horse radish peroxidase (1:10, 000, Sigma, Mo.) for another 2 h. The substrate o-phenylenediamine in the presence of $H_2O_2$ (Sigma Fast OPD tablet sets) was added (30 min incubation at room temperature) and the reaction was stopped by adding 3 M $H_2SO_4$. The visible product was detected at 490 nm on a plate reader (Dynatech MR7000).

BIAcore Immunoassay for BMP-2.

The immunoreactive BMP-2 was quantified by an immunoassay using BIAcore 2000 biosensor (Pharmacia, Uppsala, Sweden). First, a monoclonal antibody of BMP-2 (Orthogene, Fremont, Calif.) was immobilized onto a CM-5 sensor chip surface using the amine coupling kit (Pharmacia, Uppsala, Sweden). BMP-2 in the release medium was assayed over the immobilized antibody surface. Sample volume was 30 µl and HEPES-buffered saline (HBS) from Pharmacia was used as the mobile phase with a flow rate of 10 µl/min. The surface was regenerated by an injection of 10 µl of 10 mM HCl (pH 2) after each injection of BMP-2 solution. The antibody on the chip surface remained stable for more than 1 month. BMP-2 samples were analyzed based on the standard curve ranging from 50 to 1600 ng/ml BMP-2.

Bioassay for bFGF.

The biological activity of bFGF was determined by a cell proliferation assay (20). Balb/c 3T3 fibroblasts (25,000/well, CCL-163, ATCQ in Dulbecco's modified Eagle's medium (DMEM) containing 10% bovine calf serum, 50 U/ml streptomycin and 50 µg/ml penicillin were seeded (200 µl/well) on 96-well plates. The cells were grown to confluence for one week without changing the medium. On day 7, bFGF samples or standards (10 µl) in the release medium were added and followed 20 h later by addition of 1 µCi of 3H-thymidine (6.7 Ci/mmol, DuPont/NEN® Research Products, Boston, Mass.) per well. After another 6–8 h, the cells were collected on filter paper by using a PHD TM cell harvester (Cambridge Technology Inc.). The harvested cells were resuspended in 3 ml of scintillation cocktail 3a7OB (Research Products International Corp., IL) and counted (Beckman LS 1701 scintillation counter).

Results

Application of the Stabilization Strategy for bFGF Delivery.

Highly acidic pH and intermediate moisture content in the polymer microclimate are known to be deleterious conditions for most proteins (7). Therefore, neutralization of polymer microclimate pH should improve the stability of other encapsulated proteins. To test this hypothesis, we selected recombinant human basic fibroblast growth factor (bFGF), which is undergoing clinical trials. Most commonly known for its potent ability to promote anglogenesis, bFGF is a mitogen for a number of mesoderm- and neuroectoderm-derived cells such as fibroblasts, endothelial cells, smooth muscle cells, osteoblasts, and melanocytes (30). It is currently being tested for wound healing, osteogenesis, and diabetic ulcers (30). Like most therapeutic proteins, its in vivo serum half-life is very short (<3 min (31)). Any prolonged treatment (e.g., osteogenesis) could potentially benefit from the development of controlled release formulations, but bFGF has been difficult to encapsulate in biodegradable polymers. Polymer formulations that deliver bioactive bFGF have been either too short-acting (e.g., because naturally derived polymers were used (32, 33)) or have been prepared from nondegradable materials (34, 35), which require implant removal and therefore are undesirable in many clinical situations.

Before encapsulating bFGF, we considered several sources of irreversible inactivation of bFGF known to occur at neutral pH and physiological temperature. This protein belongs to a family of heparin-binding growth factors, and in the absence of heparin (or an equivalent glycosaminoglycan), it loses activity very rapidly in the presence of elevated temperature, an acidic pH, or proteolytic enzymes (36, 37). Like many proteins, bFGF adheres avidly to glass and plastic surfaces (34). Disulfide exchange of bFGF has also been reported in the presence of trace metals (e.g., those remaining from the polymerization of polymer). Based n the stability profile of bFGF and our experience with BSA, we selected five additives for encapsulation of bFGF. The combination of 3% $Mg(OH)_2$ and 15% BSA were suitable for neutralization of the acidic microclimate. The presence of BSA at high concentration may also be useful to inhibit adsorption of bFGF to PLGA (34). We added heparin at a weight ratio of 1:1 (heparin to bFGF) to enhance bFGF stability (37), and EDTA to chelate trace of heavy metals. Finally, sucrose was kept in the solid bFGF (as received from the supplier) to retain the bFGF structure in the solid state (31).

When a small amount of bFGF was encapsulated to the $Mg(OH)_2$/BSA/PLGA millicylinders (~0.0025%), the growth factor was released in a fashion similar to that observed for BSA. Over 28 days, 71% of bFGF was detected by ELISA in the release medium and 21% remained in the polymer fraction (Table 3). This accounts for about ~92% of the initially encapsulated bFGF. It is important to note that when the millicylinders did not contain both heparin and the $Mg(OH)_2$/BSA combination, bFGF lost immunoreactivity. For example, if heparin was removed from the stable formulation, only 2% bFGF was released over one month with no immunoreactive bFGF in the residual fraction (Table 3). Similarly, if 20% arabic gum was substituted for 3% $Mg(OH)_2$/15% BSA (a 0% $Mg(OH)_2$/15% BSA control could not be performed because of BSA aggregation), no bFGF was observed in the release medium after 4 days and only 38% was accounted for in both the release and residual fraction.

To increase the capacity of the polymer to deliver bFGF, we increased the bFGF loading to 0.01% and the sucrose loading to 21.3%. The bFGF release initially is much slower and later exhibits a linear release profile up to 4 weeks. The release of BSA from the same preparation in PBST was similarly retarded. This indicates that sucrose can be used to slow down the release of both BSA and bFGF from the polymer, probably by increasing the viscosity of the aqueous pores in the polymer.

The release kinetics of bFGF demonstrated that soluble bFGF is released continuously with BSA. However, immunoreactive bFGF does not guarantee bioactivity. To test the bioactivity of bFGF released from PLGA, we examined the bFGF samples in the release and residual fraction by the ability of the growth factor to induce cell proliferation (as indicated by $^3$H-thymidine incorporation (20)). The encapsulation procedure did not affect the biological activity of bFGF. Some small inactivation apparently occurred during the release experiment, but 65–85% of bFGF was bioactive over the entire release interval, confirming that the majority of immunoreactive bFGF was biolooically active. Thus, by neutralizing the acidic microclimate in PLGA, we have prepared an injectable PLGA device that delivers bioactive bFGF for more than one month.

Generality of the Use of Basic Salts to Improve Stability of Proteins Encapsulated in PLGA.

To further test the generality of the basic additive stabilization approach, we encapsulated another important growth factor, bone morphogenetic protein2 (BMP-2), in PLGA millicylinders and formulated BSA in PLGA microspheres. BMP-2, which has significant homology with transforming growth factor-β, can effectively induce bone regeneration at extraskeletal sites when implanted in a suitable carrier such as inactivated collagenous bone matrix (38). This fascinating feature makes BMP-2/carrier systems commonly studied alternatives to bone grafting (39). It has been suggested that a central problem in the application of BMP-2 for bone regeneration is the inability to slowly release the active protein homogeneously throughout the site of desired bone formation (40). PLGA is a logical choice to overcome the difficulties with the BMP-2 carriers (41).

Following the same approach as for the bFGF formulation, we used the 3% $Mg(OH)_2$/15% BSA combination to neutralize the acidic microclimate pH in PLGA millicylinders containing BMP-2 (0.25% loading). In addition, we performed a second positive control using the protein substitute, gum arabic (i.e., 3% $Mg(OH)_2$/1 5% gum arabic/0.25% BMP-2). In both cases, a controlled release of protein was observed over 28 days (data not shown) resulting in a recovery (released+soluble residue fraction) of >80% (Table 3). In contrast, when the base was removed from the formulation (18% gum arabic), only 30% protein was recovered by the immunoassay. Therefore, the stability characteristic of BMP-2 in PLGA millicylinders was very similar to that of bFGF (although additional stabilizers were used for bFGF) with and without the addition of the basic additive. For both growth factors, in the absence of basic additive, the protein was released mostly on the first day and only a small amount of protein could be recovered from the polymer after 28 days release. In the presence of the basic salt, both proteins were continuously released with >80% recoverable in the 28-day experiment. Moreover, the in vivo biological activities (angiogenesis in nude mice for the bFGF and osteogenesis in rats for the BMP-2) of the BSA/$Mg(OH)_2$-containing formulations were also confirmed when the devices were implanted subcutaneously (data not shown).

A final important consideration is the applicability of the basic additives for, protein stabilization in PLGA microspheres. Microspheres have several advantages compared to millicylinders, particularly to reduce pain of injections and to simplify administration (8). To test our approach in microspheres, we examined whether encapsulated BSA undergoes the acid-induced mechanism of instability and if so, whether the basic additive approach is effective in preventing it. As seen in Table 3, BSA also forms non-covalent aggregates (~25–75%) when encapsulated PLGA microspheres, indicating that an acidic microclimate also develops in PLGA microspheres prepared by the solvent evaporation method. (We note that in some control experiments, we also observed disulfide-bonded aggregates of BSA, but in every case, this mechanisms was secondary (<5%) to the acid-induced non-covalent mechanism). PLGA 50150 microspheres have been shown recently to form a highly acidic microclimate when prepared by this commonly used technique (25, 26, 42, 43), which is consistent with the BSA instability mechanism.

We note that it has been suggested that BSA becomes unstable in PLGA microspheres primarily by protein adsorption to the polymer (44). This conclusion was strongly weighed on the ability of SIDS to cause liberation of previously unreleasable BSA from the polymer. We remark that the SDS buffer we used in the SDS-PAGE dissolves the noncovalent aggregates formed in the polymer. This solubilization effect may explain the reported release of sequestered BSA from the polymer caused by the surfactant. Therefore, we conclude that protein adsorption, consistent with our simulations described earlier, is not the predominant source of instability of BSA in PLGA microspheres.

Whereas the mechanism of BSA instability in microspheres was similar to that observed in millicylinders, the co-encapsulation of $Mg(OH)_2$ was only marginally successful to inhibit BSA aggregation in microspheres. For example, the soluble fraction of BSA was increased from 17–25% (no base) to 39%–72% (with $Mg(OH)_2$) (Table 3). This modest increase in stability of BSA afforded by $Mg(OH)_2$ and previous microscopy studies from our group illustrating a heterogeneous pH distribution in $Mg(OH)_2$/PLGA microspheres (no protein) (24) suggests that the basic additive in microspheres could not diffuse to all the acidic protein pores in the polymer. This is likely due to lower protein loading used in microspheres compared to that in millicylinders, which decreases the number of pores in the polymer. To overcome this problem, we turned to another basic salt, $MgCO_3$, which has an equivalent basicity to $Mg(OH)_2$, but has a ~10-fold higher solubility to facilitate diffusion of the base in the polymer pores. The more soluble carbonate salt inhibited aggregation of BSA similarly to the inhibition attained in millicylinders by $Mg(OH)_2$. For the medium molecular weight PLGA (0.64 dl/g), the aggregation was held to just 13% over 28 days with 89% recovery (Table 3). Remarkably, co-encapsulation of $MgCO_3$ in the low MW PLGA (0.20 dl/g) resulted in reduction of BSA aggregation to just 1.5% over 51 days with 94% recovery (Table 3). This latter preparation controlled the release of BSA slowly and continuously over the entire experiment after a 32% burst (data not shown).

In closing, by elucidating the deleterious conditions and mechanisms of instability of BSA in PLGA delivery systems, we have been able to devise a rational procedure for stabilization of BSA. This approach was also confirmed for therapeutic growth factor encapsulated in millicylinders and BSA in microspheres. Our data strongly suggest that poorly water-soluble basic salts such as $Mg(OH)_2$ can be used to neutralize the polymer microclimate pH to levels necessary to retain the structure and biological activity of acid-labile proteins encapsulated in PLGA delivery systems.

Example 11

Stabilization of Protein in PLA-PEG Blended Microspheres

A blend of: slowly degrading poly(D, L-lactide) (PLA), to reduce the production of acidic species during protein release; and water-soluble poly(ethylene glycol) (PEG), to increase diffusion of BSA and polymer degradation products, were used to modify the microsphere microclimate and protein release behavior. PLA has a much slower degradation rate than PLGA 50/50 due to its higher hydrophobicity and the steric hindrance for the water attack of ester bond introduced by the methyl group of lactic acid (4). Slow degradation of PLA results in less production of acidic species, presumably providing a more neutral microclimate for encapsulated proteins during early incubation (5). However, slow degradation of PLA will also cause slow and discontinuous release of protein antigens and a gradual acid build-up. In addition, its strong hydrophobicity has been suggested to possibly denature proteins (6). Therefore, the second component, relatively more hydrophilic PEG, is introduced into PLA to adjust the microsphere hydrophobicity and permeability. PEG is nontoxic and soluble in numerous organic solvents and water. During release, PEG can lie soluble in the release medium, resulting in the formation of swollen structure with high water content in the polymer blend. This swollen polymer structure is expected to increase exchange of polymer degradation products with the surrounding medium, minimizing the risk of acid-induced protein degradation. Moreover, before excessive PLA degradation occurs, aqueous pores formed by PEG dissolution are expected to increase diffusion of the encapsulated protein, providing continuous protein release.

The PLA-PEG microspheres studied here were prepared by oil-in-oil emulsion and solvent extraction (O/O) method, instead of the most commonly used water-in-oil-in-water double emulsion and solvent evaporation (W/O/W) method. The former approach generally results in high protein entrapment levels and superior protein stability due to the absence of water (7,8). A model protein antigen, bovine serum albumin (BSA), was selected and encapsulated in the polymer blend.

Materials and Methods

Chemicals

Poly(D, L-lactide) with inherent viscosity of 1.07 dl/g in $CHCl_3$ was from BPI (Birmingham, Ala.). Polyethylene glycol) with molecular weight 10,000 and 35,000 was obtained from Aldrich Chem, Co. (Milwaukee, Wis.) and Fluka, respectively, Bovine serum albumin: (A-3059, Lot 32H0463) was purchased from Sigma Chemical Co. (St. Louis, Mo.). Protein molecular weight and pI standards for electrophoresis were from Pharmacia LKB (Piscataway, N1). All other biochemicals and chemicals were of analytical grade or purer and obtained from commercial suppliers.

Microsphere Preparation

The polymeric microspheres were prepared by an anhydrous O/O method. First, PLA and PEG at various weight ratios were co-dissolved in acetonitrile at a total polymer concentration of 20% (w/v). Sieved BSA (<20 μm) was suspended in acetonitrile-polymer solution and homogenized at 15,000 rpm in an ice bath, Then the antigen suspension was added drop-wise into the continuous phase (cottonseed oil containing 1.6% (W/V) span 85) stirred at 750 rpm with an overhead stirrer. After 5 hr, petroleum ether (b.p. 50–110° C.) was poured into the cottonseed oil bath to extract the remaining acetonitrile from the polymer. After an additional 15 min of stirring, the microspheres were filtered, washed with 250 ml of petroleum ether and lyophilized.

Microsphere Characterization

Morphology and Particle Size Determination

The microspheres were coated with gold-palladium by using PELCO MODEL 3 SPUTTER COATER 91000. Surface morphology of the microspheres was examined by a Philips XL Scanning Electron Microscope. Particle size was estimated by averaging diameters of 50 microspheres.

Polymer Composition Analysis by IR

The composition of microspheres prepared from different blends of PLA and PEG was analyzed by infrared spectroscopy. A Nicolet protege 460 was used to obtain the spectra (32 scans per sample, over 600–4000 cm$^{-1}$) for the samples. A series of PLA and PEG physical mixtures with different weight ratios was used to make a calibration curve. Samples were dissolved in chloroform and casted into a sodium chloride cell. The composition of the microparticles was estimated by comparing peak height ratios corresponding to the carbonyl (C=O) band of PLA at 1757 cm$^{-1}$ and the $CH_2$ band at 2876 cm$^{-1}$ due to the PEG component, and assuming a negligible content of span 85 surfactant in microspheres.

Polymer Phase Behavior Analysis by DSC

Samples (3–5 mg) were loaded into aluminum pans and DSC thermograms were recorded by a Perkin-Elmer DSC 7 Differential Scanning Calorimeter. Nitrogen gas was the sweeping gas and the heating rate was 20° C./min.

Determination of Microsphere Loading

The amount of antigen encapsulated in microspheres was determined by recovering the protein from the microspheres. First, acetone was added to the microspheres to dissolve the polymer. The mixture was vortexed, centrifuged and then supernatant was removed. After the removal of polymer was repeated three times, the remaining protein pellet was air dried and reconstituted in phosphate buffer saline pH 7.4 containing 0.02% Tween 80((PBST) and protein content was determined by the Coomassie Plus method (Pierce Chem Co., IL)

Evaluation of Model Antigen Release From Microspheres

Samples of 10 mg microspheres were suspended in 1 ml PBST. The suspension was incubated at 37° C. under mild agitation. At pre-selected intervals, release media were removed for determination and replaced with fresh buffer. The amount of protein released was assayed by the Coomassie Plus method (Pierce Chem. Co., IL). At the end of release, microspheres were collected and remaining soluble protein in the microspheres was analyzed as described in the section Determination of microsphere of loading. Any insoluble protein aggregates were collected by centrifugation and reconstituted in denaturing agent (8 M Urea or 6 M Guanidine-HCl (GnCl)). Determination of any aggregates soluble in denaturing agent gave the amount of non-covalently bonded aggregates. With the further addition of reducing agent (10 mM DTT+1 mM EDTA), any disulfide-bonded aggregates were dissolved. 'The total dissolved portion in denaturing and reducing agents gave the total amount of non-covalent and disulfide-bonded aggregates.

pH Change in the Release Medium During Release

The pH of the release medium was monitored by a Corning 430 pH meter (Corning Inc., NY) at each sampling interval.

Water Uptake of Microspheres

After incubation at 97% relative humidity and 37° C., samples were taken out and weighed immediately. The water uptake of microspheres was estimated by:

Water uptake (%)=$(W_1-W_2)/W_2 \times 100\%$

Where $W_1$ and $W_2$ are the weights of the hydrated microspheres and microspheres before incubation, respectively. No corrections were made for inter-particle water content in Wi or the water content within lyophilized microspheres in $W_2$.

Structural Analysis of Encapsulated BSA

At the end of release period, the integrity of remaining BSA in the polymer was determined by both sodium dodecyl sulfate polyacrylamide gel electrophoresis (SDS-PAGE) and isoelectric focusing (IEF) analysis, which were performed on a Pharmacia PhastSystem (Pharmacia Biotech.) according to the file no. 110 and 100 in the Phastsystem™ User Manual, respectively. In both analyses, Coomassie staining file no. 200 was used. The secondary structure of antigen samples was determined lay measuring circular dichroic (CD) spectra. The spectra were taken with a J-500A Jasco spectropolarimeter (Hachioji, Japan) at room temperature. The tertiary structure of protein samples was analyzed by measuring the intrinsic fluorescence emission spectra. Fluorescence emission spectra (300–500 nm for BSA) were obtained on a Perkin-Elmer LS50B luminescence spectrometer scanned at 240 nm/min. The excitation wavelength for BSA was set to 295 nm. Details of these procedures were as described previously (11).

Results

Microsphere Composition and Phase Behavior Analysis

The IR spectra of blank microspheres prepared from pure PEG, pure PLA (i.v.=1.07 dl/g), and a PLA/PEG displayed a broad band at 2876 cm$^{-1}$ and a peak at 1757 cm$^{-1}$ were assigned to the $CH_2$ stretching on the PEG unit and the carbonyl group (C—O) of PLA, respectively. Both characteristic peaks for $CH_2$ and C=O appeared in the IR spectrum of the blend of PLA and PEG. By estimating the PEG content in the blend with a calibration curve generated from PLA and PEG physical mixtures with different weight ratios, complete incorporation of PEG in PLA matrix by the O/O encapsulation method was indicated.

In Table 1, the DSC thermograms of prepared blank microspheres are shown. PLA exhibited a $T_g$ of roughly 53.5° C. and PEG showed a $T_m$ of 71° C. In the PLA and PEG microsphere blend, down shifts in both $T_g$ and $T_m$ of 7–11° C. and 8–10° C., respectively, were observed, indicating partial miscibility between PLA and PEG.

Microsphere Morphology

After preparation, microspheres with different weight ratios of PLA and PEG had spherical and smooth surfaces. An average size of ~100 μm was recorded for these microsphere preparations. After 35 days of incubation, microspheres prepared from 100% PLA remained intact with a smooth surface. With the blend of PEG, the microsphere structure still remained intact, but a small amount of pores appeared on the PLA/PEG microspheres surface. With higher PEG blend, more pores became visible. In addition;, the microsphere surface showed indentations, which may have occurred during drying of the particles before analysis, The SEM images suggested that the incorporation of PEG into PLA created more channels in the microspheres, which may have increased the permeability to the encapsulated protein. In addition, the microsphere surface likely consisted of a PLA-rich phase, whereas the interior of microspheres was likely PEG-rich. Otherwise, more pores created by PEG solubilization would be expected on the microsphere surface. The PLA-rich surface phenomenon is possibly due to the higher hydrophobicity and longer chain of PLA, which could have caused selective PLA precipitation at the surface during the O/O microsphere preparation. Further surface analysis would be required for a definitive conclusion.

Release Kinetics and Stability of BSA in the PLA/PEG Microspheres

To investigate the effect of PEG in the PLA/PEG microspheres, microspheres with different weight ratios of PEG 10,000 to PLA were prepared and the BSA controlled release was monitored in PBST at 37° C. Theoretical BSA loading of all these formulations was 5% and encapsulation efficiency vas invariably between 90% and 100%. When PEG content was less than 10% of polymer weight, similar release kinetics of BSA from microspheres was observed and less than 45% of BSA was released after a 4-week incubation. When PEG content was raised to 20%, the total releasable amount of protein was significantly increased to 75%. In addition, the effect of PEG molecular weight on protein release was also evaluated. BSA had almost identical release kinetics in microspheres irrespective of whether PEG 10,000 and PEG 35,000 was used (the weight ratio of PEG/PLA was 20:80). When PEG 35,000 content was increased to 30% in PLA/PEG microspheres, a higher burst release of BSA was observed.

The residual BSA remaining in these devices after the 4-week release interval (45 days for formulation without PEG, i.e., formulation o) was analyzed and listed in Table 2. For the formulation o, of the original encapsulated protein, 15% was still water-soluble and 25% of BSA had become water-insoluble aggregates in the residue. Most of the aggregates were soluble in a denaturing solvent (6 M urea), indicating their non-covalent character. When 5% of PEG was incorporated in PLA (formulation a), soluble BSA remaining in microspheres was increased to 30%, and the non-covalent aggregates were 41% of the original encapsulated BSA, When PEG content was increased to 10% (formulation b), 36% of the protein formed insoluble aggregates, Besides non-covalent aggregates, a small fraction of disulfide-bonded aggregates (soluble in 10 mM DTT) was also formed, However, no insoluble BSA aggregates were observed in formulations containing more than 20% PEG.

The integrity of the soluble BSA recovered from the polymer (28-day incubation) was further examined by SDS-PAGE. Some peptide fragments were observed in lanes 6 and 7 (formulations a and b), indicating mild peptide bond hydrolysis occurred during incubation. In contrast, soluble BSA recovered from formulations containing more than 20% PEG showed a very similar band with standard BSA and no degradation product bands were noticeable. Soluble BSA recovered from formulations c, d and e was further examined by IEF. No pI alterations in BSA were observed in these samples. Likewise, secondary and tertiary structure of BSA was similar to standard BSA control. Hence, the structure of BSA in formulations c, d, and e was retained within the polymer for one month.

Mechanisms of BSA Stabilization in the PLA/PEG Microspheres

One-month continuous release of stable BSA from microspheres was achieved when PEG content in the PLA/PEG blends was above 20%. As identified previously, an acidic microclimate and intermediate moisture levels are the two major factors which cause non-covalent aggregation and peptide-hydrolysis of BSA in PLGA 50/50 microspheres. Does the blend of PEG with PLA improve the microclimate as we designed, i.e., by avoiding the acidic microclimate and increasing the water content to stabilize BSA encapsulated in microspheres?

To address this question, we first examined the pH change of the release medium when the PLA/PEG formulations were incubated at 37° C. and PEST (pH 7.4). Unlike PLGA 50/50, which showed a dramatic pH drop in the release medium after 4-week incubation (3), both PLA and PLA/PEG formulations remained a relatively neutral pH (above 7) in the release medium over 29 days of incubation. However, a slightly lower pH in the release medium incubated with PLA/PEG formulation than that in PLA was observed (−0.1–0.2 pH units difference). This result suggested that some acidic degradation products were able to diffuse out of polymer device through the water channels formed by PEG in PLA/PEG formulation. In addition, by using a previously reported method (pH determination of polymer solution in the mixture of ACN and water) (12.), the $pa_H^*$ inside formulation d before and after 30-day incubation was determined as 6.5 and 5.4, respectively, suggesting a very small accumulation of acid in the polymer. In contrast, PLGA 50/50 microspheres were reported to reach $pa_H^*$ ~3 after similar incubation time (5). These results demonstrated that acid build-up was largely reduced in the PLA/PEG blend formulation.

The water content difference in formulations during release was compared by performing a water uptake kinetics study of microspheres at 97% relative humidity. Under controlled humidity, microspheres will adsorb water vapor and potential water uptake of different formulations during release can be predicted and compared. PEG 35,000 showed a strong water uptake. On the second day, the water content in PEG 35,000 blank microspheres was almost 120% of the dry microsphere weight. Upon blending PEG in the formulation, the water uptake rate was significantly increased. The higher the PEG content, the higher the increase in water uptake. Microspheres containing 20% PEG had almost twice the amount of water uptake; relative to those with 10% of PEG in the humid environment. When microspheres are incubated in the release medium, higher water content in the PLA/PEG blend is expected. The presence of 5% BSA did not increase water uptake rate significantly in the blend. formulation. The water uptake in the blend was likely overwhelmed by the strong water adsorption by PEG.

The above results demonstrated that a less acidic and more hydrophilic microenvironment was achieved in the PLA/PEG blend. Maintenance of a relatively neutral microclimate in PLA/PEG blend formulation can be attributed to the following. First, few acidic species were produced during early incubation due to the slow degradation of PLA. The rate constant of PLA degradation at 37° C. in water has been reported to be roughly 0.012 $day^{-1}$, much slower than PLEA 50:50, 75:25, 85:15 with rate constants of 10.55, 0.103, and 0.026 $day^{-1}$, respectively (4). In addition, prior to hydration, the polymer acid content was determined as 21 and 4.2 nmol/mg for the PLGA 50/50 used in our previous study and PLA used here, respectively (13). Therefore, the total amount of acidic species in PLA should be less than PLGA either during encapsulation or during hydration. Second, the blend of PEG with PLA significantly increased the water content in the formulation, which is expected to dilute the acidic species even further. Third, the dissolution of PEG in the release medium may create more water channels, thereby increasing the diffusion for acidic species out of the polymer and for buffering species into the PLA matrix.

By the above three mechanisms, a less acidic microclimate will be formed in the PLA/PEG blend. When PEG content is less than 10% in the blend formulations, non-covalent aggregates and peptide fragments of BSA were still observed, This is possibly due to regional acidity in the polymer which caused BSA degradation. Slowly produced polymer degradation products in certain regions can not be diluted or diffuse out of the; polymer because of insufficient water channels, resulting in regionally low ply. With increasing amount of PEG in the blend, a relatively neutral microclimate was gradually attained. Although slight pH decreases within the polymer was still detected in the blend containing 20% PEG, it was not significant enough to cause non-covalent aggregation and peptide-hydrolysis of BSA.

The stabilization of BSA in the PLA/PEG microspheres can also be attributed in part to the increased water content in the formulation. It was reported that the aggregation of BSA at acidic pH (pH=2) exhibit a pronounced bell-shape with maximum aggregation corresponding to roughly 1008 water/100 g dry protein. When water content increased to 500%–1000%, aggregation of BSA was declined sharply (14). In the blend formulation containing 20% of PEG, when incubated at 97% R.H. for 1 week, the water content in the microspheres is—25%. Assuming all the water is available for BSA (BSA loading is 5%) in microspheres, the water content of BSA is ~500%. During release, the water content in microspheres was expected to be higher than 500%. Thus, in addition to the minimal acid content, the aggregation of BSA was minimized by the high amount of imbibed water in the microenvironment.

PEG is hydrophobic in nature and it may potentially interact with the hydrophobic groups of BSA and induce BSA unfolding. It was reported that PEG of low Mw 1000 and 4000 interacts favorably with hydrophobic sides chains of human serum albumin (hSA), leading to a stabilization of the unfolded state (15). To test the interaction of high Mw PEG with BSA, GnCl unfolding curve of BSA with the addition of PEG 10,000 and PEG 35,000 (the weight ratio of BSA to PEG was 1:5) was determined by fluorescence spectroscopy. Similar unfolding curves were observed in three preparations, The conformational stability of BSA was therefore likely not affected by the addition of PEG 10,000 and PEG 35,000 with 1:5 ratio of BSA to PEG.

Conclusions

By using the PLA/PEG blend, a one-month continuous release of BSA was achieved with the absence of insoluble aggregates and peptide hydrolysis. This formulation can be used potentially for encapsulation of other acid-labile pharmaceuticals and vaccine antigens.

TABLE 1

Irreversible inactivation of BSA under simulated and encapsulated conditions at 37° C.

|  | Encapsulated[a] | Simulated[b] |
|---|---|---|
| Time to 50% aggregation | 12 days | 7 days |
| Aggregates soluble in denaturing solvent[c] | >98% | >94% |
| Peptide fragmentation[d] | 25, 40, and 55 kDa | 25, 40, and 55 kDa |

[a]15% BSA in PLGA millicylinders incubated in PBST at 37° C;
[b]lyophilized BSA at pH2 incubated under 86% R.H. at 37° C;
[c]PBST containing 6M urea and 1 mM EDTA;
[d]from SDS-PAGE of BSA samples treated with SDS and β-mercaptoethanol.

TABLE 2

Neutralization effect of $Mg(OH)_2$ on the erosion behavior of 15% BSA/PLGA millicylinders

|  | No salt | 3% $Mg(OH)_2$ |
|---|---|---|
| Non-covalent aggregates[a] % | 65 ± 8 | 2.0 ± 0.4 |
| Water uptake[b], % | 48 ± 2 | 106 ± 4 |
| PLGA degradation t½[c], days | 16.0 | 25.1 |
| PH of the medium[d] | 3.5 | 7.0 |

[a]extracted from the devices after incubation in PBST at 37° C. for 2 weeks (mean ± SEM, n = 3);
[b]determined by weighing the wet and dry devices after incubation in PBST at 37° C. for 1 weeks (mean ± SEM, n = 3);
[c]t½ is the time when the PLGA MW (determined by GPQ reduced to half of the original MW during incubation in PBST at 37° C.;
[d]PBST medium containing 5 mg polymer device after incubation at 37° C. for 4 weeks; No medium pH change was detected in either sample for the first 3 weeks.

TABLE 3

Generality of the stabilization effect of basic salts for protein delivery from PLGA

| Formulations |  | Released % | Soluble Residue[f], % | Insoluble Residue[g], % | Recovery % |
|---|---|---|---|---|---|
| BSA/ PLGA microspheres (0.64 l/g)[a] | No base | 4.4 ± 0.1[e] | 17 ± 2 | 68 ± 6 | 90 |
|  | 3% $Mg(OH)_2$ | 6.9 ± 0.2 | 65 ± 2 | 26 ± 1 | 98 |
|  | 3% $MgCO_3$ | 17 ± 2 | 59 ± 1 | 13 ± 2 | 89 |
| BSA/ PLGA microspheres (0.20 dl/g)[b] | No base | 16 ± 2 | 0.9 ± 0.1 | 24 ± 3 | 41[h] |
|  | 3% $Mg(OH)_2$ | 37 ± 2 | 2.1 ± 0.1 | 30 ± 2 | 69[h] |
|  | 3% $MgCO_3$ | 68 ± 2 | 24 ± 1 | 1.5 ± 0.2 | 94 |
| BFGF/ PLGA millicylinders[c] | 15% BSA/ 3%$Mg(OH)_2$/ no heparin 20% gum arabic/heparin 15% BSA/3% $MG(OH)_2$/ heparin | 1.9 ± 1.3 32 ± 1 71 ± 5 | 0 6 ± 3 21 ± 2 |  | 2 38 92 |
| BMP-2/ PLGA millicylinders[d] | 15% BSA/ 3%$Mg(OH)_2$ 18% Gum arabic 15% Gum arabic/ 3% $MG(OH)_2$ | 55 ± 1 24 ± 3 60 ± 9 | 25 ± 1 6 ± 1 23 ± 2 |  | 80 30 83 |

[a]BSA loading was ~4% and the release study was carried out for 28 days;
[b]BSA loading was ~4% and the release study was carried out for 51 days;
[c]bFGF loadino, was ~0.0025% and the release study was carried out for 28 days;
[d]BMP-2 loading was ~0.25% and the release study was carried out for 28 days;
[e]All the data represent mean SEM, n 3;
[f]Soluble in PBST (BSA) or in PBST/1% BSA/10 ~Lglml heparin for (bFGF and BMP-2);
[g]Insoluble in PBST but soluble in 6M urea;
[h]Less than the Computed recovery was observed in the unstable preparations.

Example 12

PLGA Microspheres which Stabilize Vincristine Sulfate (VCR)

Vincristine sulfate (VCR) and and vinblastine sulfate (VBL) are two vinca alkaloids that are commonly used as single agents or in combination for systemic treatment of AIDS-KS. VCR and VBL structurally identical with exception of the group attached to the nitrogen at position 1, at which VCR possesses a labile N-formyl group and VBL has a stable methyl group. Both drugs undergo pH-dependent degradation in aqueous solution, the pH of maximum stability is ~2 for VBL and ~4.5 for VCR. This example demonstrates that VCR becomes unstable in PLGA (50% D,L lactide content) microspheres, whereas encapsulated VBL is highly stabilized. This example provides PLGA microspheres that stabilize VCR for over a month.

Materials and Methods

Chemicals

Vincristine sulfact (98% purity) and vinblastine sulfate (97% purity) were obtained from Sigma (St. Louis, Mo.). PLGA with copolymer ratio of D,L-lactide to glycolide 50:50 and inherent viscosity of 0.23 dl/g was purchased from Birmingham Polymers (Birmingham, Ala.), $Mg(OH)_2$ was obtained from Aldrich Chemical Co. (St. Louis, Mo.) and $ZnCO_3$ was purchased from ICN Biopharmaceuticals (Aurora, Ohio). All other reagents and solvents were of analytical grade or purer and purchased from commercial suppliers. Microspheres Preparation Microspheres were prepared by a standard oil-in-oil emulsion-solvent extraction method (17). 150 mg PLGA were dissolved in 150 μl of acetonitrile (CAN) before addition of 15 μl of aqueous VCR or VBL solution (20 mg/ml). In some instances, $Mg(OH)_2$ or $ZnCO_3$ at 0.5, 3, and 10% (wt. base/wt. polymer) were suspended in the polymer solution to raise the microclimate pH inside the microspheres. The resulting solution or suspension was added drop-wise to 25 ml of oil (95% cottonseed oil and 5% Span 85 emulsifier) stirred at 500 rpm and room temperature. After 2.5 h of microsphere hardening. 40 ml of petroleum ether (bp: 50 to 100° C.) were added to the emulsion to extract CAN. The emulsion was stirred for additional 15 min, the particles were collected by filtration, and washed 3 times with petroleum ether. The hardened microspheres were flash-frozen with liquid nitrogen and lyophilized with a Labconco Freezone 6 system for 1 day.
Analysis of Drugs and Their Degradation Products by HPLC VCR and VBL were examined by high performance liquid chromatography (HPLC). The HPLC system consisted of the following: a 510 pump, a 717 Plus autosampler, and a 486 UV detector (waters, Milford, Mass.). A $C_{18}$ 3.9×150 mm reverse phase column (Waters Nova-Pak) was used at a flow rate of 1 m./min. The mobile phase was composed of aqueous solution of sodium phosphate (10 mM) and methanol 40:60 (v/v) (pH 7.0). For UV detection, the wavelength was set to 298 nm.
Identification of VCR Degradation Product by LC-MS For identification of VCR and its degradation products a LC/MS system was used. The system consisted of a Perkin-Elmer Sciex API 300 triple-quadruple mass spectrometer (Thornhill, Ontario, Canada) coupled to a Schimadzu HPLC system (Columbia, Md.). The HPLC system was equipped with an SCL-1A system controller, a LC-10A pump, a GT-104 degasser, and an SIL-10A autosampler. The separation of the parent drug and the degradation products was performed in 10 mM ammonium formate (pH 4) and CAN (40/60 v/v) on a $C_{18}$ reversed phase column.
Microscopic Evaluation of Microsphere Size Distribution and Morphology Greater than one hundred particles for each preparation were sized by sight under Zeiss Axiolab light microscope equipped with a 10× objective and a sizing scale bar. Scanning electron microscopy (SEM) images of PLGA microspheres were obtained by using a Philips XL30 field emission gun scanning electron microscope. Samples were coated with conductive gold prior to analysis.
Evaluation of VCR and its Degradation Products During Release Drug release from microspheres was carried out in PBS (127 mM NaCl, 3 mM KCl, 8 mM $Na_2HPO_4$, 1 mM $KH_2PO_4$, pH 7.4) containing Tween 80 (0.02% w/w/) (PBST) at 37° C. under perfect sink conditions. VCR and VBL were unstable in the release media so release kinetics was monitored indirectly from the drug remaining in the polymer. Microspheres were weighed and dissolved in a 50% (v/v) ACN water solution. The precipitated polymer and salts were spun down by brief centrifugation. An aliquot of the supernatant containing drug was removed and analyzed by HPLC.

Non-Aqueous Solvent pH Measurements 150 mg of PLGA were dissolved in 40 μl CAN and $ZnCO_3$, and $Mg(OH)_2$ was suspended in the polymer solution at 0.5, 3, and 10% 9 w. base/wt. polymer). 15 μl of double distilled water were added to the suspension and vortexed for 20 s to simulate microsphere preparation conditions. The undissolved salts were spun down by a brief centrifugation and the supernatant was diluted in an $CAN:H_2O$ mixture to make a 50 mg/ml polymer concentration. The final solvent composition was 80:20 (v/v) $CAN:H_2O$. The pH was measured with a Corning Semi-Micro Combination glass pH-electrode attached to a Corning pH meter (VWR scientific, PA). As described previously (19), the actual proton activity in the organic solution mixture (a__)was calculated from the pH meter reading (pH) by pa__=pH–δ, where δ is a correction coefficient which equals 0.95 for an $ACN:H_2O$ 80:20 (v/v) mixture.

Results

Degradation of VCR Encapsulated in PLGA Microspheres

Microspheres containing 0.22% (w/w) drug were obtained by an oil-in-oil emulsion-solvent extraction technique. The encapsulation efficiency was ~91% (Table 1, Protocol A). Microspheres were spherical in shape with the mean particle size of 46 μm.

All the encapsulated vincristine was originally preserved in its native form following encapsulation. During microsphere incubation, the drug degraded rapidly inside the particles. The appearance of a major degradation product was observed in the chromatogram (peak II,). Only 23% of drug remained in its native form after 14 days of the incubation. Curve fitting assuming pseudo-first order kinetics for the degradation of encapsulated VCR gave a rate constant of $k=1.07 \ 10^{-6} x^{-1}$ and $t_{12}=7.5$ days at 37° C.

In order to improve drug stability in the formulation, the following methodology was used (20): (a) identification of the degradation product, (b) elucidation of the cause and mechanism of VCR degradation in the PLGA, and (c) stabilization of VCR in PLGA microspheres by inhibiting or bypassing the cause and mechanism of VCR degradation.
Identification of the VCR Degradation Product The degradation product was more hydrophobic relative to the parent drug since its retention time (peak II at 7.6 min) was longer than the retention time of VCR (peak I at 5.5 min). LC-MS analysis revealed the main molecular peaks of 797.5 Da for the degradation product and 825.5 Da for VCR. The difference of 28 Da was likely due to the loss of N-formyl group at the position 1. Formation of the deformyl derivative of VCR was reported previously by Sethi et al. (18) and is favorable at acidic pH 921). The retention time of the degradation product formed in PLGA microspheres also corresponds to the retention time of VCR degradation product formed in solutions pH 1.5 915). it is well established

TABLE 1

Characterization of Microspheres

| Protocol code | Drug added | Base added | Base loading, % (w/w) | Drug loading % (w/w)[a] | Encapsulation efficiency, %[a] | Particle size, μm[b] | Yield, % |
|---|---|---|---|---|---|---|---|
| A | VCR | — | — | 0.22 ± 0.01 | 91 ± 1 | 46 ± 3 | 89 |
| B | VBL | — | — | 0.18 ± 0.01 | 88 ± 3 | 50 ± 2 | 93 |
| C | VCR | $Mg(OH)_2$ | 0.5 | 0.15 ± 0.02 | 76 ± 8 | 42 ± 3 | 91 |
| D | VCR | $Mg(OH)_2$ | 3 | 0.272 ± 0.01 | 98 ± 1 | 59 ± 4 | 87 |
| E | VCR | $Mg(OH)_2$ | 10 | 0.18 ± 0.01 | 94 ± 1 | 50 ± 3 | 94 |
| F | VCR | $ZnCO_3$ | 3 | 0.15 ± 0.01 | 82 ± 3 | 52 ± 3 | 89 |
| G | VCR | $ZnCO_3$ | 10 | 0.19 ± 0.02 | 87 ± 5 | 43 ± 5 | 92 |

[a]N = 3 ± SD.
[b]N = 100 ± SEM.

Co-Encapsulation of $Mg(OH)_2$ in PLGA Microspheres Stabilizes VCR

The encapsulation of insoluble bases in PLGA microspheres causes an increase in the microclimate pH (19) and an inhibition of acid-induced instability of encapsulated proteins (20,23). To inhibit acidic degradation of VCR, $Mg(OH)_2$ was co-encapsulated in PLGA microspheres at 0.5, 3 and 10% (wt. base/wt. Polymer) loading. The addition of base did not change the spherical appearance of microspheres, although the particle surface at high base content became less smooth due to protruding base particles. A microsphere particle size of 50 μm, a loading of ~0.2%, and an encapsulated efficiency in a range of 76 to 98% were obtained (Table 1, Protocols C–E).

The acidic degradation of VCR was fully inhibited by addition of 3 and 10% of $Mg(OH)_2$ the deformyl degradation product appeared after 2 weeks of incubation. This can be attributed to non-homogeneity of microclimate neutralization by $Mg(OH)_2$ (19) and/or an insufficient supply of base for the neutralization of acidic groups formed as PLGA hydrolysis proceeded.

Despite VCR stabilization during release, the addition of $Mg(OH)_2$ induced the appearance of a second degradation product formed during microspere preparation (peak III). The degradation product was more hydrophilic with a retention time of 2.6 min compared to 5.5 min for VCR. The retention time of peak III is consistent with that of the VCR degradation product formed in solution in pH ~7.3 in the study by Vendrig et al. (15). Roughly 12% of the drug was degraded during the preparation of the microspheres containing 3 and 10% $Mg(OH)_2$. No further formation of the basic degradation product was observed during microspere incubation. It is probable that VCR is either exposed to a higher pH or is more reactive in the polymer-base solutions during microspere preparation than in the polymer microclimate during incubation.

Substitution of $Mg(OH)_2$ With $ZnCO_3$ Inhibits Alkaline Degradation

To inhibit formation of the basic degradation product a weaker base, $ZnCO_3$ and 9.8 for $Mg(OH)_2$ (23). The hydronium ion activities in non-aqueous solvents (pa_) of the polymer solutions with and without bases were measured to evaluate the conditions affecting VCR stability during microspere preparation (Table 2). The pa_ of PLGA solution containing no additives was low at 3.9. This value increased with addition of 0.5, 3, and 10% of $Mg(OH)_2$ to 4.8, 6.1 and 7.3, respectively. The addition of $ZnCO_3$ also increased pa_ but to a lesser extent than the addition of $Mg(OH)_2$ on a weight basis.

The substitution of $Mg(OH)_2$ with $ZnCO_3$ did not change the physical characteristics of the microspheres. Sperical microspheres with ~0.17% drug loading, 85% encapsulation efficiency, and the ~48 μm particle size were obtained (Table 1, Protocols F–G,). However, only 3% of VCR converted to the basic product during microsphere preparation with $ZnCO_3$ compared to 12% with $Mg(OH)_2$. The acid-catalyzed VCR degradation was inhibited resulting in 97% of the drug remaining intact after 3 weeks and 92% intact after 4 weeks. Hence, the substitution of $Mg(OH)_2$ with $ZnCO_3$ further improved the stability of encapsulated VCR in PLGA microspheres.

Drug Release Kinetics

Drugs were released in sustained manner from all the formulations. VBL microspheres released drug nearly linearly for 4 weeks (66% of encapsulated drug released). The VCR formulations contained 3 and 10% $ZnCO_3$ and released 56 and 31% of the stable drug, respectively, at the end of incubation period. VCR was released faster from the formulation containing more $ZnCO_3$, probably because the co-encapsulation of this based increased polymer water content leading to a faster drug transport. The water content of PLGA usually increases with co-encapsulation of basic additives and microclimate neutralization (23). For example, the water content was reported to increase 2.5 and 4 times by co-encapsulation of 3% $Mg(OH)_2$ and 3% $ZnCO_3$, respectively, for PLGA millicylinders containing 15% protein (23). Hence, we expected to observe an increase in VCR release rate from the formulations containing bases compared formulations containing bases compared to the formulations without base. However, just the opposite was observed as less drug was released after 28 days from the microspheres containing either 3–10% $Mg(OH)_2$ or 3% $ZnCO_3$ compared to microspheres without additives. A possible explanation is that the solubility of weakly basic drug decreased in the neutralized microclimate (VCR) has $pK_a$s of 5 and 7.4 (24)). In addition, the positively charge drug may have interacted with the negatively charged polymer end-groups, which become ionized in the neutralized microenvironment.

TABLE 2

Neutralization of PLGA Solutions with Basic Salts

| Base added | Base loading, % (w/w) | pa_ |
|---|---|---|
| — | — | 3.9 ± 0.1 |
| $Mg(OH)_2$ | 0.5 | 4.8 ± 0.3 |
| $Mg(OH)_2$ | 3 | 6.1 ± 0.4 |
| $Mg(OH)_2$ | 10 | 7.3 ± 0.2 |
| $ZnCO_3$ | 3 | 5.0 ± 0.1 |
| $ZnCO_3$ | 10 | 6.4 ± 0.3 |

[a]N = 5 ± SD.

What is claimed is:

1. A method of preparing a biodegradable polymeric delivery system for delivering a biologically active agent to a subject, wherein the biodegradable polymeric delivery system maintains a pH of greater than 3 during biodegradation of the polymeric delivery system over a period of 4 weeks, comprising:
   a) forming a polymer solution comprising a solvent and a poly(lactide-co-glycolide) (PLGA) polymer which comprises from 50% to 100% lactide or lactic acid and from 50% to 0% glycolide or glycolic acid, wherein said lactide or lactic acid is selected from the group consisting of the L isomer, the D isomer, or a D,L racemic mixture;
   b) optionally blending from 10% to 30% of one or more pore-forming agents with the PLGA polymer solution of step (a);
   c) dispersing from 0.50% to 20% (w/w) of one or more basic additives wherein the basic additive has a solubility in water of from about $1.24 \times 10^{-13}$ to about $3.16 \times 10^{-3}$ and a pH of about 6.82 to about 9.76 for a saturated aqueous solution, in the polymer solution;
   d) dispersing from 0.1% to 20% (w/w) of a composition comprising the agent or the agent plus carrier in the polymer solution; and
   e) solidifying the polymer from the resulting polymer solution to provide a biodegradable polymeric system whose microclimate maintains a pH of greater than 3 during biodegradation of the polymeric system for at least 4 weeks.

2. The method of claim 1 wherein the polymer solution comprises 50% lactide or lactic acid and 50% glycolide or glycolic acid.

3. The method of claim 1 wherein the polymer solution comprises from 40 to 1200 mg/ml of the polymer in organic solvent.

4. The method of claim 1 wherein the basic additive is magnesium carbonate.

5. The method of claim 1 wherein the composition of step c comprises a carrier.

6. The method of claim 4 wherein the carrier is selected from the group consisting of albumin, gum arabic, gelatin, dextran, a water soluble amino acid, a monosaccharide, a disaccharide, and combinations thereof.

7. The method of claim 1 wherein from 0.5 to 3.0% (w/w) of the basic additive is dispersed in the polymer solution and wherein from 5% to 20% (w/w) of the agent or a composition comprising the agent and carrier is dispersed in the polymer solution.

8. The method of claim 1 wherein from 0.5 to 3.0% (w/w) of the basic additive is dispersed in the polymer solution and wherein from 5% to 30% (w/w) of a pore forming agent is dispersed in the polymer solution.

9. The method of claim 1 wherein from 0.5 to 3.0% (w/w) of the basic additive is dispersed in a polymer solution comprising from 40 to 300 mg/ml of polymer in organic solvent.

10. The method of claim 1 wherein from 3.0 to 20% of the basic additive is dispersed in the polymer solution, wherein the polymer comprises lactide and glycolide, and wherein the polymer has an inherent viscosity of 0.7 dl/g or greater.

11. The method of claim 1 wherein from 3.0 to 20% of the basic additive is dispersed in the polymer solution comprising from 200 mg/ml to 1200 mg/ml of polymer in organic solvent.

12. A method of preparing a biodegradable polymeric delivery system for delivering a biologically active agent to a subject, wherein the biodegradable polymeric delivery system maintains a pH of greater than 3 during biodegradation of the polymeric delivery system over a period of 4 weeks, comprising:
   a) forming a polymer solution comprising a solvent and a biodegradable polymer which produces acids during biodegradation;
   b) dispersing the agent in the polymer solution;
   c) dispersing one or more basic additives selected from the group consisting of magnesium carbonate, magnesium hydroxide, magnesium oxide, magnesium trisilicate, zinc carbonate, zinc hydroxide, zinc phosphate, aluminum hydroxide, basic aluminum carbonate, dihydroxyaluminum sodium carbonate, dihydroxyaluminum aminoacetate, calcium phosphate, calcium carbonate, magaldrate in the polymer solution; and
   d) solidifying the polymer from the resulting polymer solution to provide a biodegradable polymeric system whose microclimate maintains a pH of greater than 3 during biodegradation of the polymeric system for at least 4 weeks.

13. The method of claim 12 further comprising the step of dispersing a pore-forming agent in the polymer solution of step (a).

14. The method of claim 13 wherein the basic additive is selected from the group consisting of magnesium carbonate, magnesium hydroxide, calcium carbonate, zinc hydroxide, and zinc carbonate.

15. A biodegradable polymeric delivery system for delivering biologically active agents encapsulated therein to a subject, wherein the biodegradable polymeric delivery system maintains a pH of greater than 3 during biodegradation of the polymeric delivery system over a period of 4 weeks, wherein said delivery system comprises
   a) a PLGA polymer
   b) from 0.5% to 20% by weight of a composition which comprises the agent or a combination of the agent and a carrier; and
   c) from 0.5% to 20% by weight of one or more basic additives selected from the group consisting of magnesium carbonate, magnesium hydroxide, magnesium oxide, magnesium trisilicate, zinc carbonate, zinc hydroxide, zinc phosphate, aluminum hydroxide, basic aluminum carbonate, dihydroxyaluminum sodium carbonate, dihydroxyaluminum aminoacetate, calcium phosphate, calcium hydroxide, magaldrate; and
   d) a microclimate which maintains a pH of greater than 3 during biodegradation of the polymeric delivery system for a period of 4 weeks.

16. The delivery system of claim 15 wherein the PLGA polymer comprises 50% D,L lactide or lactic acid and 50% glycolide or glycolic acid.

17. The delivery system of claim 16 wherein the agent is selected from the group consisting of bone morphogenic protein-2, fibroblast growth factor, and tissue plasminogen activator (tPA).

18. The delivery system of claim 15 wherein the delivery system is in the form of a millicylinder, wherein the agent is bone morphogenic protein-2, and wherein the basic additive is magnesium hydroxide, zinc carbonate, or magnesium carbonate.

19. The delivery system of claim 15 wherein the delivery system is in the form of a microsphere, wherein the agent is bone morphogenic protein 2, wherein the composition comprises a carrier, and wherein the basic additive is selected from the group consisting of magnesium carbonate, magnesium hydroxide, calcium hydroxide, zinc hydroxide, and zinc carbonate.

20. The biodegradable polymeric delivery system of claim 15 further comprising 10%–30% of a pore-forming agent.

21. The biodegradable polymeric delivery system of claim 20 wherein the polymeric delivery system maintains biologically active molecules in the microclimate for a period of at least 4 weeks.

22. A method of preparing a biodegradable polymeric delivery system for delivering a biologically active agent to a subject, wherein the biodegradable polymeric delivery system is capable of stabilizing BSA encapsulated therein during biodegradation of the polymeric delivery system over a period of 4 weeks, comprising:

a) forming a polymer solution comprising a solvent and a biodegradable polymer which produces acid during biodegradation;
  b) optionally blending from 10% to 30% of a pore-forming agent with the polymer solution of step (a);
  c) dispersing from 0.5% to 20% (w/w) of a basic additive wherein the basic additive has a solubility in water of from about $1.24 \times 10^{-13}$ to about $3.16 \times 10^{-3}$ and a pH of about 6.82 to about 9.76 for a saturated aqueous solution, in the polymer solution;
  d) dispersing from 0.1% to 20% (w/w) of a composition comprising the agent or the agent plus carrier in the polymer solution; and
  e) solidifying the polymer from the resulting polymer solution to provide a biodegradable polymeric system wherein less than 15% of the total BSA in the polymer forms insoluble aggregates after incubation in physiological buffer at 37° C. for 4 weeks.

23. The polymeric delivery system prepared by the method of claim 22.

24. The polymeric delivery system of claim 23 wherein the polymer is a PLGA polymer which comprising from 50% to 100% lactide or lactic acid and from 50% to 0% glycolide or glycolic acid, wherein said lactide or lactic acid is selected from the group consisting of the L isomer, the D isomer, or a D,L racemic mixture.

25. The method of claim 1 wherein the biodegradable polymeric system maintains a pH of greater than 3 during biodegradation of the polymeric system for at least 51 days.

26. The method of claim 12 wherein the biodegradable polymeric delivery system maintains a pH of greater than 3 during biodegradation of the polymeric delivery system over a period of 51 days.

27. The method of claim 15 wherein said microclimate maintains a pH of greater than 3 during biodegradation of the polymeric delivery system for a period of 51 days.

28. The method of claim 1 wherein from 0.5 to about 6% (w/w) of the basic additive is dispersed in the polymer solution and wherein from 5% to 20% (w/w) of the agent or a composition comprising the agent and carrier is dispersed in the polymer solution.

29. The method of claim 1 wherein from 0.5 to about 6% (w/w) of the basic additive is dispersed in the polymer solution and wherein from 5% to 30% (w/w) of a pore forming agent is dispersed in the polymer solution.

30. The method of claim 1 wherein from 0.5 to about 6% (w/w) of the basic additive is dispersed in a polymer solution comprising from 40 to 300 mg/ml of polymer in organic solvent.

31. The method of claim 22 wherein the biodegradable polymeric delivery system is capable of stabilizing BSA encapsulated at a level of about 3 to about 20% (w/w).

\* \* \* \* \*

UNITED STATES PATENT AND TRADEMARK OFFICE
CERTIFICATE OF CORRECTION

PATENT NO. : 6,743,446 B2
APPLICATION NO. : 09/738961
DATED : June 1, 2004
INVENTOR(S) : Schwendeman et al.

It is certified that error appears in the above-identified patent and that said Letters Patent is hereby corrected as shown below:

Column 3, last line: please delete "Table I" and replace with --Table 1--

Column 7, Example 1, line 58: please delete "JEF" and replace with --IEF--

Column 9, line 7: please delete "15%1" and replace with --15%--

Column 10, Example 3, last sentence in 2nd paragraph: please delete "(Table 1)" and replace with --(Table 2)--

Column 10, line 65: please delete "[14]"

Column 10, line 66: please delete "[14]"

Column 11, line 66: please delete "Poly(d,1-lactide-co-glycollde)" and replace with --Poly(DL-lactide-co-glycollde)--

Column 11, line 66: please delete "poly(d,1-" and replace with --poly(DL- --

Column 13, line 2: please delete "P1GA50/50" and replace with --PLGA50/50--

Column 13, line 16: please delete "P1GA" and replace with --PLGA--

Column 14, Table 5: please rename "Table 5" as --Table 4--

Column 15, Table 6: please rename "Table 6" as --Table 5--

Column 16, line 19: please delete "(>91%; Table 5)." and replace with --(>91%; Table 6).--

Column 16, line 48: please delete "(>90%; Table 6)." and replace with --(>90%; Table 7).--

Column 16, Table 6: please rename "Table 6" as --Table 7--

Column 18, line 2: please delete "ration" and replace with --ratio ~--

Column 18, line 34: please delete "(Table 7)" and replace with --(Table 8)--

Column 18, Table 7: please rename "Table 7" as --Table 8--

Column 19, line 10: please delete "(Table 8)" and replace with --(Table 9)--

UNITED STATES PATENT AND TRADEMARK OFFICE
CERTIFICATE OF CORRECTION

PATENT NO. : 6,743,446 B2
APPLICATION NO. : 09/738961
DATED : June 1, 2004
INVENTOR(S) : Schwendeman et al.

It is certified that error appears in the above-identified patent and that said Letters Patent is hereby corrected as shown below:

Column 19, Table 8: please rename "Table 8" as --Table 9--

Column 19, Example 9: please rename "Example 9" as --Example 7--

Column 20, example 10: please rename "Example 10" as --Example 8--

Column 20, line 10: please delete "50150" and replace with --50/50--

Column 20, line 28: please delete "(13)"

Column 20, line 50: please delete "(14)"

Column 21, line 36: please delete "(14)"

Column 21, line 47: please delete "(15)"

Column 21, line 52: please delete "(16)"

Column 21, line 56: please delete "(17)"

Column 22, line 10: please delete "(18, 19)"

Column 22, line 41: please delete "(20)"

Column 22, line 61: please delete "(7)"

Column 23, line 3: please delete "(30)"

Column 23, line 5: please delete "(30)"

Column 23, line 6: please delete "(31)"

Column 23, line 12: please delete "(32, 33)"

Column 23, line 13: please delete "(34, 35)"

Column 23, line 23: please delete "(36, 37)"

Column 23, line 24: please delete "(34)"

UNITED STATES PATENT AND TRADEMARK OFFICE
CERTIFICATE OF CORRECTION

| | | |
|---|---|---|
| PATENT NO. | : 6,743,446 B2 | |
| APPLICATION NO. | : 09/738961 | |
| DATED | : June 1, 2004 | |
| INVENTOR(S) | : Schwendeman et al. | |

It is certified that error appears in the above-identified patent and that said Letters Patent is hereby corrected as shown below:

Column 23, line 27: please delete "n" and replace with --on--

Column 23, line 33: please delete "(34)"

Column 23, line 34: please delete "(37)"

Column 23, line 37: please delete "(31)"

Column 23, line 43: please delete "(Table 3)" and replace with --(Table 12)--

Column 23, line 50: please delete "(Table 3)" and replace with --(Table 12)--

Column 24, line 4: please delete "(20)"

Column 24, line 17: please delete "proteln2" and replace with --proteln-2--

Column 24, line 22: please delete "(38)"

Column 24, line 24: please delete "(39)"

Column 24, line 28: please delete "(40)"

Column 24, line 29: please delete "(41)"

Column 24, line 35: please delete "1 5%" and replace with --15%--

Column 24, line 39: please delete "(Table 3)" and replace with --(Table 12)--

Column 24, line 60: please delete "(8)"

Column 24, line 64: please delete "Table 3" and replace with --Table 12--

Column 25, line 5: please delete "50150" and replace with --50/50--

Column 25, line 7: please delete "(25, 26, 42, 43)"

Column 25, line 11: please delete "(44)"

Column 25, line 26: please delete "(Table 3)"

UNITED STATES PATENT AND TRADEMARK OFFICE
CERTIFICATE OF CORRECTION

PATENT NO. : 6,743,446 B2
APPLICATION NO. : 09/738961
DATED : June 1, 2004
INVENTOR(S) : Schwendeman et al.

It is certified that error appears in the above-identified patent and that said Letters Patent is hereby corrected as shown below:

Column 25, line 30: please delete "(24)"

Column 25, line 43: please delete "(Table 3)" and replace with --(Table 12)--

Column 25, line 46: please delete "(Table 3)" and replace with --(Table 12)--

Column 25, Example 11: please rename "Example 11" as --Example 9--

Column 26, line 6: please delete "(4)"

Column 26, line 9: please delete "(5)"

Column 26, line 13: please delete "(6)"

Column 26, line 33: please delete "(7, 8)"

Column 26, line 46: please delete "N1" and replace with --NJ--

Column 27, line 62: please delete "Wi" and replace with --W1--

Column 28, line 15: please delete "(11)"

Column 28, line 29: please delete "In Table 1, the" and replace with --The--

Column 29, line 14: please delete "and listed in Table 2"

Column 29, line 60: please delete "(3)"

Column 30, line 3: please delete "(12)"

Column 30, line 8: please delete "(5)"

Column 30, line 40: please delete "(4)"

Column 30, line 43: please delete "(13)"

Column 31, line 6: please delete "(14)"

Column 31, line 8: please delete "-25%" and replace with --25%--

UNITED STATES PATENT AND TRADEMARK OFFICE
CERTIFICATE OF CORRECTION

PATENT NO. : 6,743,446 B2
APPLICATION NO. : 09/738961
DATED : June 1, 2004
INVENTOR(S) : Schwendeman et al.

It is certified that error appears in the above-identified patent and that said Letters Patent is hereby corrected as shown below:

Column 31, line 10: please delete "-500%" and replace with --500%--

Column 31, Table 1: please rename "Table 1" as --Table 10--

Column 31, Table 2: please rename "Table 2" as --Table 11--

Column 32, Table 3: please rename "Table 3" as --Table 12--

Column 32, Example 12: please rename "Example 12" as --Example 10--

Column 33, line 7: please delete "(17)"

Column 34, line 21: please delete "(19)"

Column 34, Results, line 32: please delete "(Table 1," replace with --(Table 13,--

Column 34, Results, line 47: please delete "(20)"

Column 34, line 63: please delete "(18)"

Column 34, last sentence: please delete "915). it is well estab-lished" and replace with --.--

Column 35, Table 1: please rename "Table 1" as --Table 13--

Column 35, line 20: please delete "(19)"

Column 35, line 22: please delete "(20,23)"

Column 35, line 29: please delete "(Table 1," and replace with --(Table 13,--

Column 35, line 34: please delete "(19)"

Column 35, line 43: please delete "(15)"

Column 35, line 54: please delete "(23)"

Column 35, line 58: please delete "(Table 2)" and replace with --(Table 14)--

Column 35, last line: please delete "1," and replace with --13,--

UNITED STATES PATENT AND TRADEMARK OFFICE
CERTIFICATE OF CORRECTION

| | |
|---|---|
| PATENT NO. | : 6,743,446 B2 |
| APPLICATION NO. | : 09/738961 |
| DATED | : June 1, 2004 |
| INVENTOR(S) | : Schwendeman et al. |

It is certified that error appears in the above-identified patent and that said Letters Patent is hereby corrected as shown below:

Column 36, line 36: please delete "(23)"

Column 36, line 40: please delete "(23)"

Column 36, line 49: please delete "(24)"

Column 36, Table 2: please rename "Table 2" as --Table 14--

Signed and Sealed this

Nineteenth Day of August, 2008

JON W. DUDAS
*Director of the United States Patent and Trademark Office*